(12) United States Patent
Trost et al.

(10) Patent No.: US 10,117,771 B2
(45) Date of Patent: Nov. 6, 2018

(54) PENILE TRACTION DEVICES

(71) Applicants: Mayo Foundation for Medical Education and Research, Rochester, MN (US); PathRight Medical Inc., Wayzata, MN (US)

(72) Inventors: Landon W. Trost, Rochester, MN (US); Zachary M. Hoffman, Bloomington, MN (US); David Talen, Plymouth, MN (US); Jason Gerold, Shakopee, MN (US)

(73) Assignees: Mayo Foundation for Medical Education and Research, Rochester, MN (US); PathRight Medical Inc., Wayzata, MN (US)

( * ) Notice: Subject to any disclaimer, the term of this patent is extended or adjusted under 35 U.S.C. 154(b) by 191 days.

(21) Appl. No.: 15/040,364

(22) Filed: Feb. 10, 2016

(65) Prior Publication Data

US 2016/0235580 A1    Aug. 18, 2016

Related U.S. Application Data

(60) Provisional application No. 62/197,323, filed on Jul. 27, 2015, provisional application No. 62/115,246, filed on Feb. 12, 2015.

(51) Int. Cl.
*A61F 5/00* (2006.01)
*A61F 5/41* (2006.01)

(52) U.S. Cl.
CPC .......... *A61F 5/41* (2013.01); *A61F 2005/411* (2013.01)

(58) Field of Classification Search
CPC ............................. A61F 5/41; A61F 2005/411
USPC ...................................................... 600/38–41
See application file for complete search history.

(56) References Cited

U.S. PATENT DOCUMENTS

| | | | | |
|---|---|---|---|---|
| 8,734,324 | B2 * | 5/2014 | Muller | A61F 5/41 600/39 |
| 2004/0215055 | A1 * | 10/2004 | Gomez-de-Diego | A61F 5/41 600/38 |
| 2011/0213201 | A1 * | 9/2011 | Moon | A61F 5/41 600/38 |
| 2012/0130158 | A1 | 5/2012 | Deitch et al. | |

OTHER PUBLICATIONS

Arafa et al., "The prevalence of Peyronie's disease in diabetic patients with erectile dysfunction," *Int J Impot Res.*, 19(2):213-217, Epub Aug. 17, 2006.

Chung et al., "Penile traction therapy and Peyronie's disease: a state of art review of the current literature," *Ther Adv Urol.*, 5(1):59-65, Feb. 2013.

Dalkin et al., "Potent men undergoing radical prostatectomy: a prospective study measuring sexual health outcomes and the impact of erectile dysfunction treatments," *Urol Oncol.*, 26(3):281-285, Epub Nov. 7, 2007.

(Continued)

*Primary Examiner* — John Lacyk
(74) *Attorney, Agent, or Firm* — Fish & Richardson P.C.

(57) ABSTRACT

Devices and methods for treating penile aberrations include the use of traction devices. For example, this document describes devices and methods for applying longitudinal and/or contralateral penile traction forces to treat anatomical aberrations related to Peyronie's disease and other conditions.

18 Claims, 18 Drawing Sheets

(56) References Cited

OTHER PUBLICATIONS

Dibenedetti et al., "A Population-Based Study of Peyronie's Disease: Prevalence and Treatment Patterns in the United States," *Adv Urol.*, 2011:282503. Epub Oct. 23, 2011.

La Pera et al., "Peyronie's disease: prevalence and association with cigarette smoking. A multicenter population-based study in men aged 50-69 years," *Eur Urol.*, 40(5):525-530, Nov. 2001.

Lindsay et al., "The incidence of Peyronie's disease in Rochester, Minnesota, 1950 through 1984," *J Urol.*, 146(4):1007-1009, Oct. 1991.

Martinez-Salamanca et al., "Acute phase Peyronie's disease management with traction device: a nonrandomized prospective controlled trial with ultrasound correlation," *J Sex Med.*, 11(2):506-515, Epub Nov. 22, 2013.

Mulhall et al., "Subjective and objective analysis of the prevalence of Peyronie's disease in a population of men presenting for prostate cancer screening," *J Urol.*, 171(6 Pt 1):2350-2353, Jun. 2004.

Rhoden et al., "Prevalence of Peyronie's disease in men over 50-y-old from Southern Brazil," *Int J Impot Res.*, 13(5):291-293, Oct. 2001.

Rybak et al., "A retrospective comparative study of traction therapy vs. no traction following tunica albuginea plication or partial excision and grafting for Peyronie's disease: measured lengths and patient perceptions," *J Sex Med.*, 9(9):2396-2403, Epub Aug. 17, 2012.

Schwarzer et al., "The prevalence of Peyronie's disease: results of a large survey," *BJU Int.*, 88(7):727-730, Nov. 2001.

\* cited by examiner

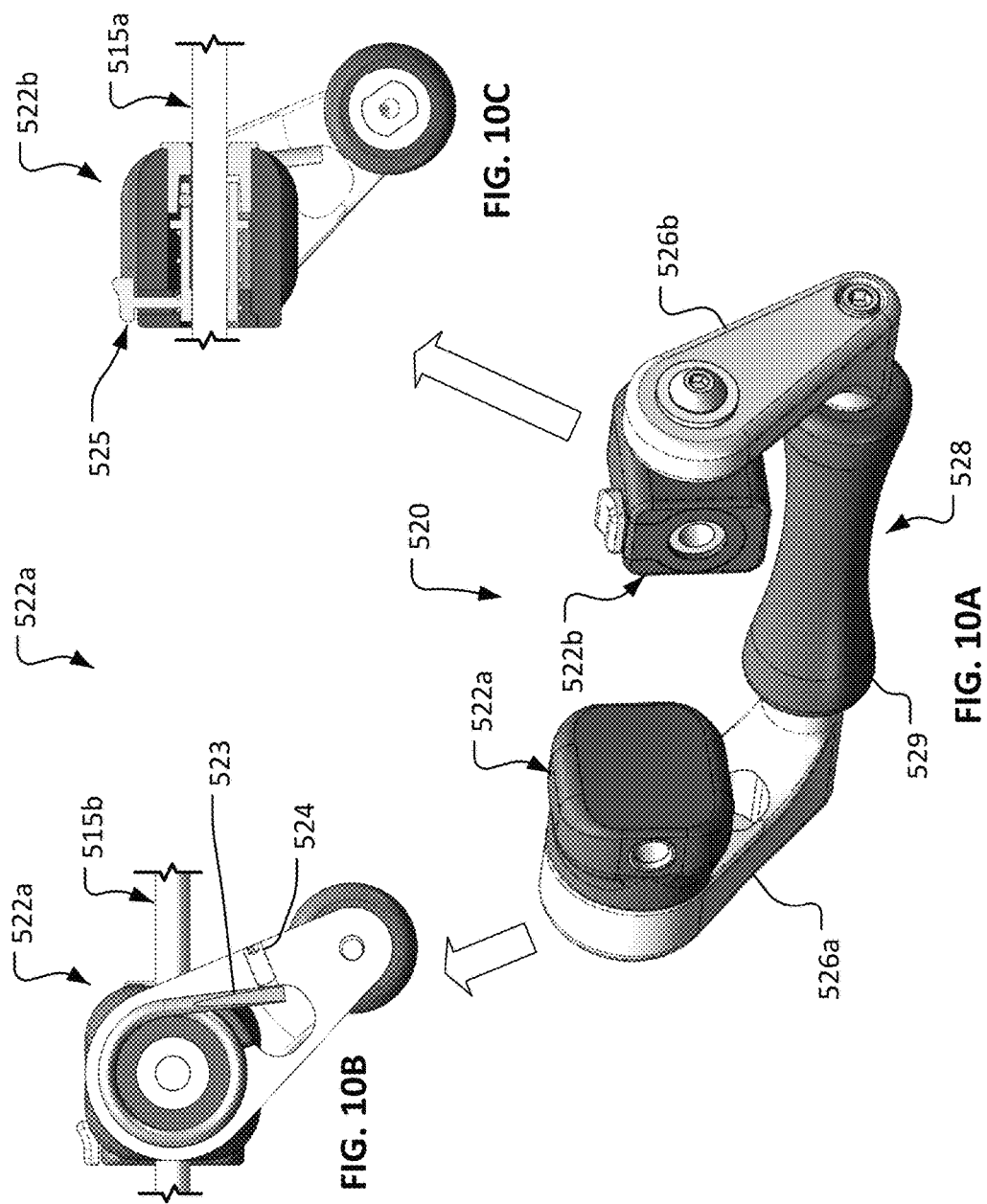

PENILE TRACTION DEVICES

CROSS-REFERENCE TO RELATED APPLICATIONS

This application claims the benefit of U.S. Provisional Application Ser. No. 62/197,323, filed Jul. 27, 2015 and U.S. Provisional Application Ser. No. 62/115,246, filed Feb. 12, 2015. The disclosures of the prior applications are considered part of (and are incorporated by reference in) the disclosure of this application.

BACKGROUND

1. Technical Field

This document relates to devices and methods for treating penile aberrations. For example, this document relates to devices and methods for applying longitudinal and/or contralateral penile traction forces to treat anatomical aberrations related to Peyronie's disease and other conditions.

2. Background Information

Peyronie's disease is the development of fibrous scar tissue inside the penis that causes curved, painful erections. In some cases, Peyronie's disease causes a significant bend or pain. This can prevent a man from having sex or might make it difficult to get or maintain an erection (erectile dysfunction or ED). For many men, Peyronie's disease also causes stress and anxiety. In a small percentage of men, Peyronie's disease goes away on its own. But in most cases, it will remain stable or worsen. Treatment might be needed if the curvature is severe enough that it prevents successful sexual intercourse.

Peyronie's disease signs and symptoms might appear suddenly or develop gradually. The most common signs and symptoms of Peyronie's disease include: scar tissue that can be felt under the skin of the penis as flat lumps or a band of hard tissue, a significant bend to the penis, a narrowing or an hourglass appearance, problems attaining or maintaining an erection, shortening of the penis, and pain, with or without an erection.

SUMMARY

This document provides devices and methods for treating penile aberrations. For example, this document provides devices and methods for applying longitudinal and/or contralateral penile traction forces to treat anatomical aberrations related to Peyronie's disease and other conditions.

In one implementation, a penile traction device for applying traction force to a penis of a human body includes a base configured for interfacing with the human body while the traction force from the penile traction device is being applied to the penis, a frame extending from the base, a lateral traction member coupled to the frame and configured for applying a lateral traction force to the penis, and a tensioning assembly coupled to the frame. The tensioning assembly couples with the penis such that a longitudinal traction force can be applied by the tensioning assembly to the penis.

Such a penile traction device may optionally include one or more of the following features. The base may have a clearance hole through which the penis can extend. The base may have a cushioned interface with the human body. The lateral traction member may be a roller. The lateral traction member may include a concaved surface. The frame may be reconfigurable into two or more different configurations. The frame may include distance indicators. The device may further comprise a tension indicator that provides an indication of quantity of the longitudinal traction force. The tensioning assembly may be adjustable such that the longitudinal traction force can be adjusted to two or more different tension levels.

In another implementation, penile traction device for applying traction force to a penis of a human body includes a proximal portion and a distal portion. The proximal portion is pivotable in relation to the distal portion in order to apply a lateral traction force to the penis. The proximal portion may comprise a proximal splint which is extendable and may apply longitudinal traction and force. A proximal clamp may be present and may be configured to both secure and subsequently release the penis from the proximal splint. The distal portion comprises a distal splint and a distal clamp. The distal clamp is configured to secure the penis with the distal splint and allow for subsequent release.

Such a penile traction device may optionally include one or more of the following features. The device may further comprise a tensioner that biases the distal splint to pivot in relation to the proximal splint. The tensioner may be a spring or an elastic member. The device may further comprise a tension indicator that provides an indication of the amount of tension provided by the tensioner. The tensioner may be adjustable such that the lateral traction force can be adjusted by adjusting the tensioner. The device may further comprise a proximal pad coupled to the proximal splint and that contacts the penis when the penis is secured with the proximal splint. The device may further comprise a distal pad coupled to the distal splint that contacts the penis when the penis is secured with the distal splint.

In another implementation, a method of applying one or more types of traction force to a penis includes coupling a device of any one of the aforementioned implementations to the penis, and applying the one or more types of traction force to the penis using the device.

In another implementation, a penile traction device for applying traction force to a penis of a human body includes a base configured for abutting an abdominal wall surface of the human body; a stationary hub affixed to, or integral with, the base; a rotatable wheel movably coupled with the stationary hub and movable in relation to the stationary hub, the rotatable wheel configured to releasably engage with the penis; and a clamp movably coupled with the rotatable wheel and configured for applying a clamping force to maintain a position of the penis in relation to the rotatable wheel.

Such a penile traction device for applying traction force to a penis of a human body may optionally include one or more of the following features. The device may further include a ratchet mechanism between the stationary hub and the rotatable wheel. The ratchet mechanism may be configured to maintain multiple relative positions between the stationary hub and the rotatable wheel to thereby apply various amounts of tensile force to the penis while the penis is engaged with the rotatable wheel and the base is abutting the abdominal wall surface of the human body. The device may further include, coupled to the penile traction device, one or more indicators for providing an indication of tensile force or relative position between the stationary hub and the rotatable wheel.

Particular embodiments of the subject matter described in this document can be implemented to realize one or more of the following advantages. In some embodiments, the devices described herein are configured to concurrently apply longitudinal and lateral traction forces. Hence, reduction of penile curvature and increase in penile length can result from the use of a single traction device. In some embodiments, the devices described herein are configured for applying progressive mechanical traction. That is, the devices are adjustable so as to progressively add traction forces to allow for gradual and on-going anatomical improvements. In some embodiments, the devices described herein are configured to exert traction forces that are readily adjustable and quantifiable. Hence, definitive treatment plans can be ordered and implemented, thereby potentially enhancing patient results. In addition, in some embodiments the devices described herein are configured to allow measurement and tracking of anatomical improvements over time. Such features can provide feedback regarding patient compliance and results to the treatment provider and give the patient motivation to adhere to the treatment protocol. In some embodiments, the devices described herein can be used advantageously in conjunction with a pharmacological agent as part of a treatment plan for Peyronie's disease and other conditions.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 10A is a perspective view of a tensioner subassembly of the penile traction device of FIG. 7.

FIGS. 10B and 10C are side views of portions of the tensioner subassembly of FIG. 10A.

Like reference numbers represent corresponding parts throughout.

DETAILED DESCRIPTION

Figure 1:
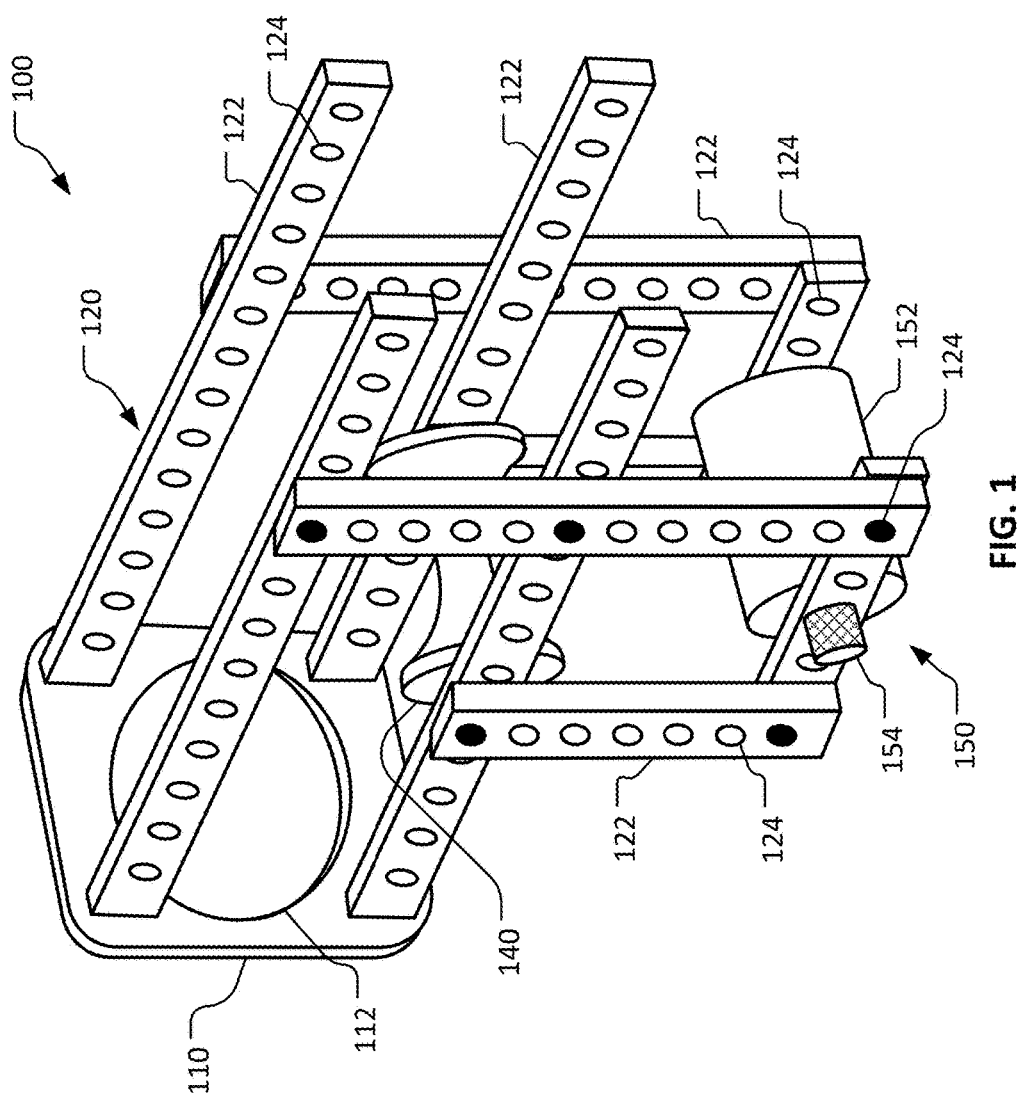
FIG. 1 is a perspective view of an example penile traction device in accordance with some embodiments provided herein.

This document provides devices and methods for treating penile aberrations. For example, this document provides devices and methods for applying longitudinal and/or contralateral penile traction forces to treat anatomical aberrations related to Peyronie's disease and other conditions. For example, the devices provided herein can be used for treatment of decreased penile length pertaining to Peyronie's disease. Further, treatment directed to penile curvature reduction while undergoing intralesional therapies for Peyronie's disease can be delivered using the devices and methods provided herein. In some circumstances, the devices provided herein are beneficial for use pre-operatively or during post-operative recovery following surgical treatment of Peyronie's disease or other urological conditions such as prostate cancer.

In general, the treatment algorithm for Peyronie's disease can include the use of a penile traction device. The goal of such therapy is to increase penile length or at a minimum restore length that was previously lost to the disease state. This is useful in men with Peyronie's disease, as a loss of penile length is commonly one of their biggest complaints. Traction therapy can be used in all phases of treatment including prior to or following surgery, during or after injection treatments, or as a stand-alone therapy.

There are also other indications for the use of penile traction therapy. One such use is for reducing penile curvature, either as a standalone therapy or in combination with injections and/or surgery. The known currently available traction devices do not permit contralateral application of force, and hence, they are only applying force in the longitudinal direction. Another indication for the penile traction devices provided herein would be for men scheduled to undergo placement of a penile prosthesis. Use of a penile traction device may increase the overall length of the patient's anatomy possible allowing for a larger prosthesis to be inserted, and also potentially make the surgery itself easier. A third indication is to use the traction devices as a stand-alone therapy. Many men complain of decreased penile length, particularly among those experiencing erectile dysfunction from any one of several known contributing conditions (diabetes, following prostatectomy, vascular disease, and others), and this therapy has been shown to increase length without need for other procedures.

The devices described herein will address Peyronie's without treatment, Peyronie's with intralesional treatment, or even patients seeking a restoration or enhancement of penile length. In addition, the devices provided herein can be useful for applying penile traction in combination with a drug regimen (e.g., XIAFLEX®) to treat penile curvature.

As described further below, in some embodiments the traction force(s) applied are dynamic loads. That is, as the penis stretches in response to the traction force(s), the traction force(s) continue to be applied. This is in contrast to stretching and holding the traction force(s) applicators (e.g., clamp) at a fixed location(s).

Figure 2:
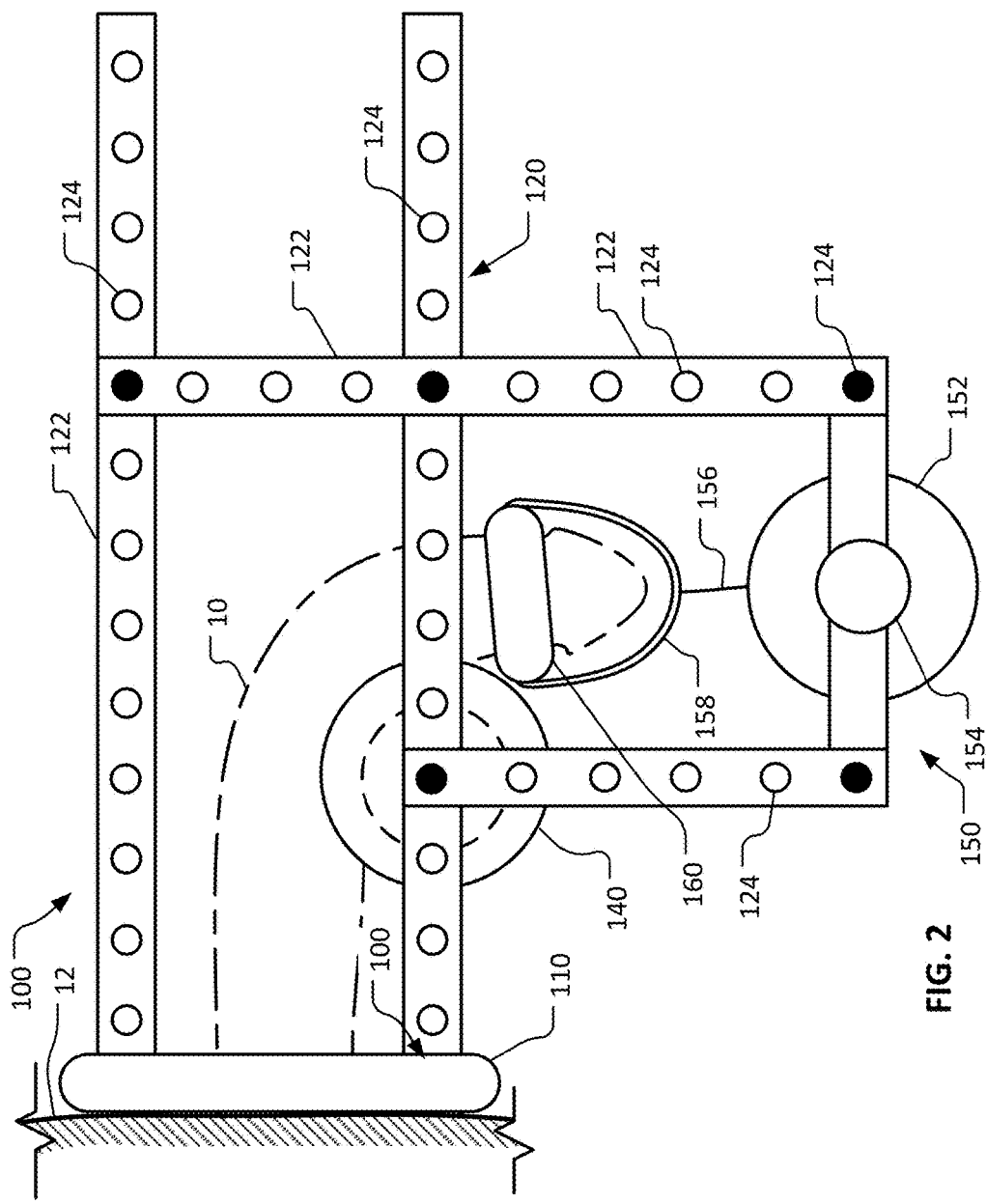
FIG. 2 is a side view of the penile traction device of FIG. 1.

With reference to FIGS. 1 and 2, a human penis 10 is depicted as undergoing a treatment for penile aberrations using an example penile traction device 100 in accordance with some embodiments provided herein. Such aberrations may be related to, but are not necessarily exclusively related to, Peyronie's disease. In some implementations, the aberrations of penis may be, but are not limited to, decreased penile length and/or excessive penile curvature. Penile traction device 100 is configurable to treat both conditions, i.e., to treat both decreased penile length and/or excessive penile curvature. Penile traction device 100 is also configurable to treat either one of decreased penile length or excessive penile curvature.

In the depicted embodiment, penile traction device 100 includes components such as a base 110, a frame 120, a lateral traction member 140, and a tensioning assembly 150. Frame 120 is rigidly coupled to base 110. In some embodiments, lateral traction member 140 is removably coupled to frame 120. In some embodiments, tensioning assembly 150 is removably coupled to frame 120. In some embodiments, lateral traction member 140 is fixedly coupled to frame 120. In some embodiments, tensioning assembly 150 is fixedly coupled to frame 120.

Frame 120 is designed to be adjustably configurable into multiple different configurations to thereby provide a traction force treatment as desired. It should be understood that the depicted embodiment of penile traction device 100 illustrates just one configuration in which the components of penile traction device 100 can be arranged.

Frame 120 is comprised of various frame members 122. Frame members 122 are attachable to each other using attachment features 124. In general, each frame member 122 includes multiple attachment features 124. One skilled in the art can recognize that any of the attachment features 124 of two or more frame members 122 can be matched and coupled together. Accordingly, frame members 122 can be coupled together (and later uncoupled and recoupled) to form many different configurations of penile traction device 100.

In depicted embodiment, attachment features 124 are holes that facilitate the use of threaded fasteners to couple frame members 122 together. However, in some embodiments other types of attachment features 124 are included. In some embodiments, attachment features 124 facilitate snapping frame members 122 together. For example, in some embodiments compressible pins can be used to facilitate pressing or snapping frame members 122 together.

In another embodiment, attachment features 124 comprise collars with detent pins. The collars can slide on frame members 122, and can be locked in any one of multiple locations along the frame members 122 as desired. The collar's detent pins can seat into recesses or holes on frame members 122.

In some embodiments, frame members 122 are made of plastic. Some example plastics that can be used to construct frame members 122 include, but are not limited to, polystyrene, acrylonitrile butadiene styrene, polyvinyl chloride, polyethylene, high density polyethylene, low density polyethylene, polypropylene, polycarbonate, polyphenelyne ether, polyamide (PA or Nylon), ultra high molecular weight polyethylene, polyimide, polyetherimide, polyphenylene sulfide, polyurethane, polyetheretherketone, thermoplastic copolyether (PEBAX), and Fluorinated Ethylene Propylene.

Alternatively, frame members 122 can be made of metals such as aluminum, stainless steel, titanium, and the like, and alloys thereof. Further, in some embodiments coated metals are used for frame members 122. For example, in some embodiments silicon-coated aluminum is used as the construct for frame members 122. It should be understood that the forgoing materials are just some example materials that can be used to make frame members 122, and that other materials are also within the envisioned scope of this disclosure.

In some embodiments, frame members 122 can be cut, trimmed, snapped-off, and the like, to a desired length. In some embodiments, frame members 122 are malleable such that they can be bent into a desired shape. In some embodiments, various types of frame members 122 are used to construct penile traction device 100 or variations thereof. Such style differences can include lengths/widths/thicknesses of frame members 122, types of attachment features 124, materials of construction, and the like. In some embodiments, a unitary style of frame members 122 is used to construct penile traction device 100 or variations thereof.

In some embodiments, frame members 122 include one or more markings, graduations, or other types of indicators thereon. Such indicators can be used to assist with the initial configuring of penile traction device 100. In addition, the indicators can be used to track progress of the traction treatments.

Base 110 is configured to press against the male body 12 as a pelvic interface. Base 110 may be made of, for example, any of the plastics or metals listed above in reference to frame members 112. In addition, in some embodiments surface padding or cushioning is included on the side that contacts male body 12. Such cushioning may be made of materials such as, but not limited to, foam rubber, silicone, nitrile, polyurethane, latex, and the like. In some embodiments, the cushioning is configured as one or more pads, and the pads are removable/replaceable.

In some embodiments, base 110 is generally planar. In some embodiments, base 110 is curved or contoured to provide a comfortable interface with male body 12. In some embodiments, base 110 is bendable to customize the contour of base 110.

Base 110 includes a clearance hole 112 through which penis 10 extends. While in the depicted embodiment clearance hole 112 is an oval, in some embodiments clearance hole 112 is circular, rectangular, or another shape.

In the depicted embodiment, penile traction device 100 includes lateral traction member 140. In some embodiments, lateral traction member 140 is a roller that can rotate in relation to frame members 122. In some embodiments, lateral traction member 140 is stationary in relation to frame members 122.

In the depicted embodiment, lateral traction member 140 is a concaved roller that essentially cradles a portion of penis 10. Lateral traction member 140 can be made of any of the materials listed above in reference to frame members 112. In addition, lateral traction member 140 can include one or more cushioning members such as described above in reference to base 110.

Lateral traction member 140 can be made and available in various configurations. For example, lateral traction member 140 can be made and available in various degrees of concavity, softness, diameters, and the like.

It should be understood that lateral traction member 140 can be mounted to frame members 122 at various locations. For example, in some implementations lateral traction member 140 can be mounted to frame 120 closer to base 110 than depicted. In some implementations, lateral traction member 140 can be mounted to frame 120 farther away from base 110 than depicted.

Because penile curvatures can be in any direction (e.g., up, down, left, right), penile traction device 100 is configured to be oriented in any desired arrangement with penis 10, and to provide traction force via lateral traction member 140 that is counter-lateral to any direction of curvature. That is, penile traction device 100 is universally configurable to treat any direction of penile curvature with counter-lateral traction force from lateral traction member 140.

While in the depicted embodiment, penis 10 is being bent in essentially a 90° angle, penile traction device 100 can be configured to provide bends of greater than or less than 90°. For example, in some embodiments penile traction device 100 can be configured to provide penile bends in a range from about 40° to about 60°, or from about 50° to about 70°, or from about 60° to about 80°, or from about 70° to about 90°, or from about 80° to about 100°, or from about 90° to about 110°, or from about 45° to about 90°.

In some embodiments, penile traction device 100 is configured without a lateral traction member 140. That is, in some embodiments only longitudinal traction forces are applied, without any lateral traction forces as would be provided by lateral traction member 140.

Penile traction device 100 includes tensioning assembly 150. Tensioning assembly 150 can be mounted essentially anywhere on frame 120. Tensioning assembly 150 includes a tension source 152, a tension adjustment 154, a tension member 156, a yoke 158, and a collar 160. It should be understood that the depicted embodiment of tensioning assembly 150 is just one non-limiting example, and that other embodiments are also envisioned within the scope of this disclosure.

Tensioning assembly 150 includes tension source 152. Tension source 152 can be a variety of different mechanisms. For example, in some embodiments tension source 152 is a ratchet device. In some embodiments, tension source 152 includes a torsion spring that can be used to apply tension to tension member 156. In some embodiments, tension source 152 can be a spring balancer that exerts an adjustable amount of tension that is consistent regardless of the extension distance of tension member 156. In some embodiments, tension source 152 is a threaded screw-like device, or a gear and/or gear train device.

Tensioning assembly 150 includes tension adjustment 154. Tension adjustment 154 is used to adjust the amount of tension applied by tension source 152 to tension member 156. In the depicted embodiment, tension adjustment 154 is a knob that can be turned to adjust the tension on tension member 156. In some embodiments, tension adjustment 154 can locked to releasably fix the tension source 152 in a particular setting. In some embodiments, tension adjustment 154 is a ratchet device.

While not depicted in this embodiment of penile traction device 100, in some embodiments a tension indicator is included. The tension indicator can provide an indication of the amount of tension that tension source 152 is applying to tension member 156 and, in turn, to penis 10. In some embodiments, the tension indicator comprises a strain gauge and a digital readout. In some embodiments, the tension indicator comprises a mechanical device such as a spring gauge that displays the tension on a dial indicator. In some embodiments, other types of tension indicators are included.

Tensioning assembly 150 includes tension member 156. Tension member 156 is coupled between tension source 152 and yoke 158. Tension member 156 transmits tension for traction therebetween. Tension member 156 can comprise a flexible or semi-flexible cord, cable, wire, and the like. In some embodiments, tension member 156 is elastic. In some embodiments, tension member 156 is non-elastic. In some embodiments, tension member 156 is a flexible gear rack that meshes with a gear of tension source 152.

Tension member 156 is coupled to yoke 158. Yoke 158 defines an interior space in which the head of penis 10 can reside. In some embodiments, yoke 158 is a Y-shaped member. In some embodiments, yoke 158 is a cup-shaped member. Yoke 158 can be a plastic or metallic member, or a combination thereof.

Yoke 158 is coupled to collar 160. Collar 160 releasably engages with penis 10 adjacent to the head of penis 10. Collar 160 can apply a tension force to penis 10. Accordingly, collar 160 is padded. In some embodiments, collar 160 is a padded clamp with an inner diameter that is smaller than the outer diameter of the head of penis 10. In some embodiments, collar 160 has a textured or sticky inner diameter surface. In some embodiments, collar 160 is adjustable in diameter. In some embodiments, different sizes of collar 160 and/or yoke 158 can be coupled with tension member 156, so as to provide a proper fit with penis 10.

While the forgoing description of penile traction device 100 contains many specific implementation details, these should not be construed as limitations on the scope of penile traction device 100 or of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Figure 3:
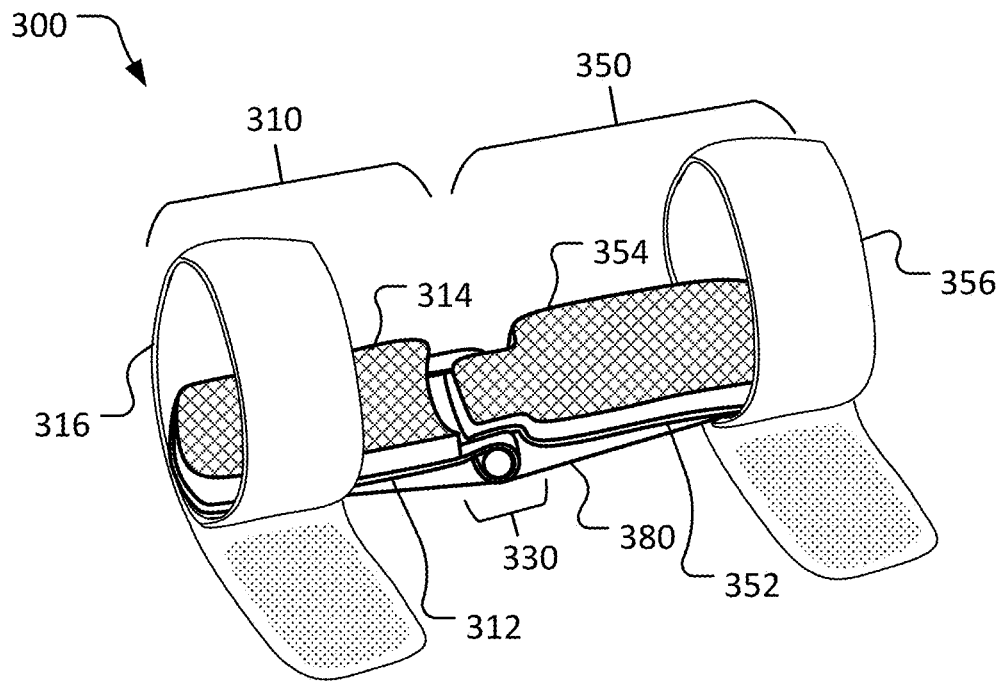
FIG. 3 is a perspective view of another example penile traction device in accordance with some embodiments provided herein.
Figure 4:
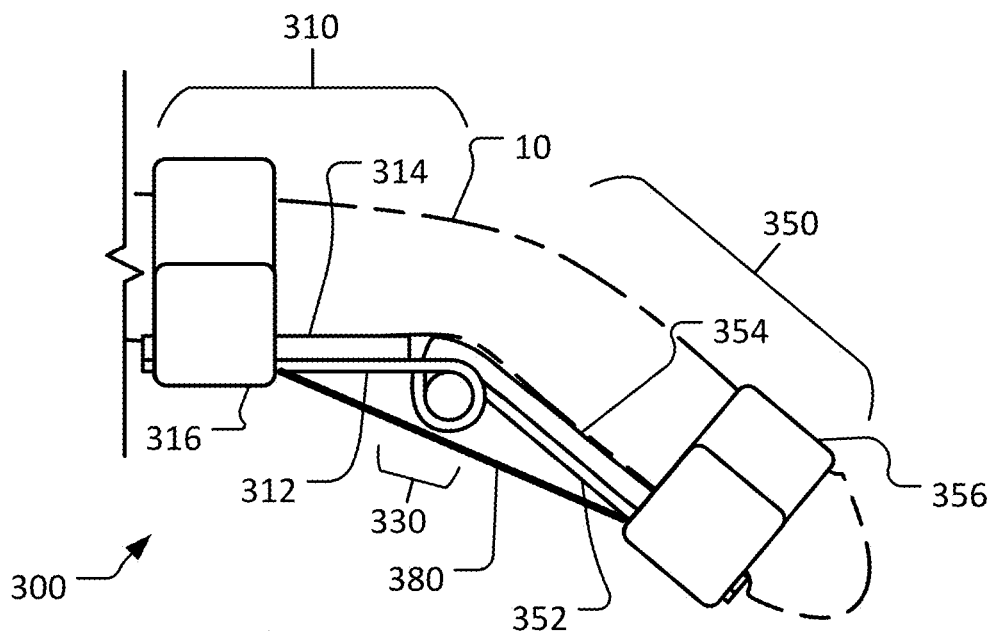
FIG. 4 is a side view of the penile traction device of FIG. 3.

Referring to FIGS. 3 and 4, a human penis 10 is depicted as undergoing a treatment for penile aberrations using an example penile traction device 300 in accordance with some embodiments provided herein. Such aberrations may be related to, but are not necessarily exclusively related to, Peyronie's disease. In some implementations, the aberrations of penis may be, but are not limited to, decreased penile length and/or excessive to penile curvature. Penile traction device 300 is configurable to be especially well-suited to treat excessive penile curvature.

In the depicted embodiment, penile traction device 300 includes a proximal portion 310 and a distal portion 350. Proximal portion 310 and distal portion 350 are pivotably coupled at a pivotable portion 330. Pivotable portion 330 allows proximal portion 310 and distal portion 350 to pivot in relation to each other. Accordingly, penile traction device 300 can apply a contralateral traction force on penis 10 to thereby treat excessive penile curvature. It should be understood that penile traction device 300 can be oriented in any position on penis 10 to thereby apply contralateral traction force in any direction (up, down, right, left, and anywhere therebetween).

In some embodiments, pivotable portion 330 comprises a malleable portion. As such, the malleable pivotable portion 330 can be bent to a desired angle, and subsequently re-bent to a different (greater or lesser) angle as desired.

While in the depicted embodiment, penis 10 is being bent in about a 30° angle, penile traction device 300 can be configured to provide bends of greater than or less than 30°. For example, in some embodiments penile traction device 100 can be configured to provide penile bends in a range from about 0° to about 20°, or from about 10° to about 30°, or from about 20° to about 40°, or from about 30° to about 50°, or 40° to about 60°, or from about 50° to about 70°, or from about 60° to about 80°, or from about 70° to about 90°, or from about 80° to about 100°, or from about 90° to about 110°, or from about 0° to about 45°, or from about 45° to about 90°, or from about 0° to about 90°, or from about 0° to about 120°.

In the depicted embodiment, penile traction device 300 also includes a tensioner 380. In the depicted embodiment, tensioner 380 is an elastic member 380. Elastic member 380 is attached at a first end to the proximal portion 310 and at a second end to the distal portion 350. Accordingly, elastic member 380 biases proximal portion 310 and distal portion 350 to pivot in relation to each other, and to thereby apply a contralateral traction force on penis 10 as desired.

While in the depicted embodiment tensioner 380 is an elastic member, in some embodiments tensioner 380 can be other types devices. For example, in some embodiments tensioner 380 is a spring (e.g., torsion spring, extension spring, leaf spring, and the like). In some embodiments, tensioner 380 can comprise a ratcheting mechanism. It should be understood that tensioner 380 can be coupled to penile traction device 300 in manners in addition to the depicted manner, such as by being built within pivotable portion 330.

In some embodiments, tensioner 380 is adjustable. For example, in some embodiments elastic member 380 can be tightened, loosened, or otherwise made to have a greater or lesser modulus of elasticity. In some embodiments, elastic member 380 comprises one or more rubber bands. In such cases, additional rubber bands can be added to increase the tension applied by tensioner 380. In some embodiments, tensioner 380 is a spring that can be adjusted by adding or removing preloading.

In some embodiments, the amount of force applied by tensioner 380 is quantifiable and identified to the user so that the user can set the amount of force to a particular quantified level. In some such embodiments, a strain gauge and a digital readout can be included as part of penile traction device 300. In some such embodiments, a dial indicator gauge can be included to indicate the amount of force applied by tensioner 380.

Proximal portion 310 includes a proximal splint 312, a proximal pad 314, and a proximal clamp 316. Proximal splint 312 is coupled to pivotable portion 330. Proximal pad 314 is attached to proximal splint 312. Proximal clamp 316 is attached to proximal splint 312.

Proximal splint 312 provides a rigid or semi-rigid structural form for proximal portion 310. Proximal splint 312 can be made of any of the materials listed above in reference to 122, including various types of plastic and metallic materials. In some embodiments, proximal splint 312 is longitudinally concaved to cradle penis 10 therein. In some embodiments, proximal splint 312 is malleable so that it can be bent into a desired configuration.

Proximal portion 310 also includes proximal pad 314. Proximal pad 314 is a cushioned material that provides a comfortable interface between proximal splint 312 and penis 10. Proximal pad 314 can be made of any of the materials listed above such as, but not limited to, foam rubber, silicone, nitrile, polyurethane, latex, and the like. In some embodiments, proximal pad 314 is configured as one or more pads. In some embodiments, proximal pad 314 is/are removable and replaceable. In some embodiments, proximal pad 314 is available in different materials, thicknesses, contours, textures, durometers, and other such properties to suit different uses, conditions, and anatomies.

Proximal portion 310 also includes proximal clamp 316. Proximal clamp 316 releasably couples penis 10 to proximal portion 310. For example, in some embodiments proximal clamp 316 is wrapped around penis 10 and attached to itself or proximal splint 312. In some embodiments, proximal clamp 316 is attached to itself or proximal splint 312 using techniques such as, but not limited to, a hook and loop fastener, resealable adhesive, a spring clamp, a snap-lock closure clamp, Proximal clamp 316 is cushioned and/or made of or lined with a soft material in some embodiments. In some embodiments, proximal clamp 316 is adjustable in diameter. In some embodiments, different sizes of proximal clamp 316 can be coupled with proximal splint 312, so as to provide a customizable proper fit with penis 10.

Distal portion 350 includes a distal splint 352, a distal pad 354, and a distal clamp 356. Distal splint 352 is coupled to pivotable portion 330. Distal pad 354 is attached to distal splint 352. Distal clamp 356 is attached to distal splint 352.

Distal splint 352 provides a rigid or semi-rigid structural form for distal portion 350. Distal splint 352 can be made of any of the materials listed above in reference to 122, including various types of plastic and metallic materials. In some embodiments, distal splint 352 is longitudinally concaved to cradle penis 10 therein. In some embodiments, distal splint 352 is malleable so that it can be bent into a desired configuration.

Penile traction device 300, and/or components thereof, can be made available in different sizes. For example, proximal splint 312 and distal splint 352 can be available in different lengths so as to be able to customize penile traction device 300 depending on where the curvature is located and the overall length of penis 10. In some embodiments, penile traction device 300 can be disassembled and reassembled by a user or clinician so as to be able to customize penile traction device 300.

Distal portion 350 also includes distal pad 354. Distal pad 354 is a cushioned material that provides a comfortable interface between distal splint 352 and penis 10. Distal pad 354 can be made of any of the materials listed above such as, but not limited to, foam rubber, silicone, nitrile, polyurethane, latex, and the like. In some embodiments, distal pad 354 is configured as one or more pads. In some embodiments, distal pad 354 is/are removable and replaceable. In some embodiments, distal pad 354 is available in different materials, thicknesses, contours, textures, durometers, and other such properties to suit different uses, conditions, and anatomies.

Distal portion 350 also includes distal clamp 356. Distal clamp 356 releasably couples penis 10 to distal portion 350. For example, in some embodiments distal clamp 356 is wrapped around penis 10 and attached to itself or to distal splint 352. In some embodiments, distal clamp 356 is attached to itself or to distal splint 352 using techniques such as, but not limited to, a hook and loop fastener, resealable adhesive, a spring clamp, a snap-lock closure clamp, Distal clamp 356 is cushioned and/or made of or lined with a soft material in some embodiments. In some embodiments, distal clamp 356 is adjustable in diameter. In some embodiments, different sizes of distal clamp 356 can be coupled with distal splint 352, so as to provide a customizable proper fit with penis 10.

In some embodiments, penile traction device 300 can be adapted to include a mechanism for applying a longitudinal traction force to penis 10.

Figure 6:
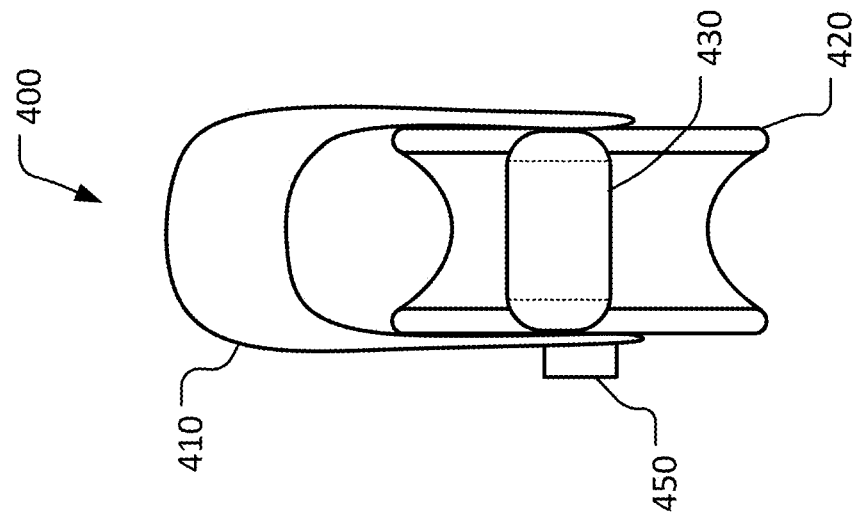
FIG. 6 is an end view of the penile traction device of FIG. 5.
Figure 5:
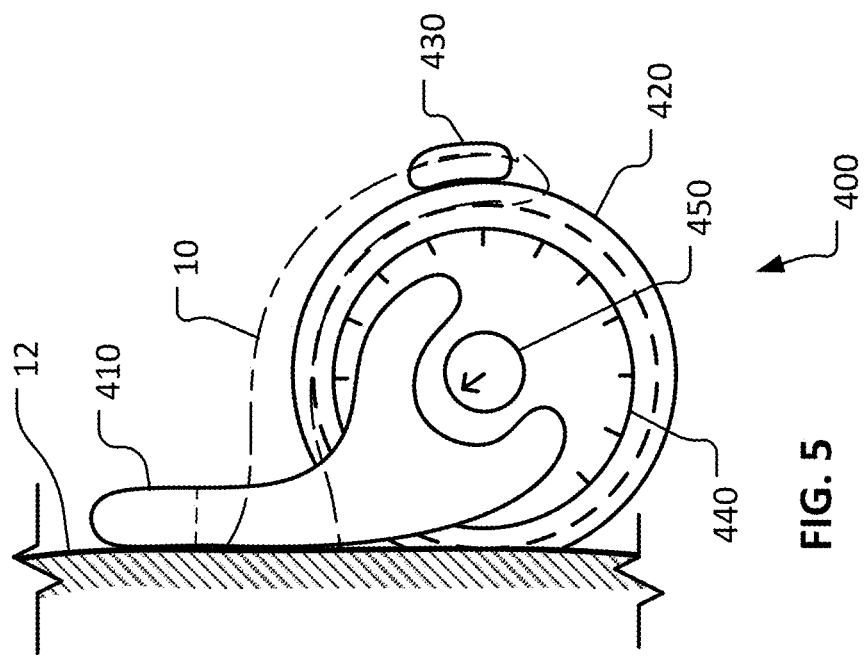
FIG. 5 is a side view of another example penile traction device in accordance with some embodiments provided herein.

Referring to FIGS. 5 and 6, a human penis 10 is depicted as undergoing a treatment for penile aberrations using an example penile traction device 400 in accordance with some embodiments provided herein. Such aberrations may be related to, but are not necessarily exclusively related to, Peyronie's disease. In some implementations, the aberrations of penis 10 may be, but are not limited to, decreased penile length and/or excessive to penile curvature. Penile traction device 400 is configurable to be especially well-suited to apply tensile traction forces to thereby provide penile length enhancement treatments. In some embodiments, penile traction device 400 is configured so that it can be discreetly worn under the clothes of a patient-user.

It should be understood that the design of penile traction device 400 is scalable to a variety of different sizes. For example, penile traction device 400 can be made in a range of sizes such that a patient-user may start with a first size and later progress to one or more larger sizes. All such sizes are within the scope of this disclosure.

In the depicted embodiment, penile traction device 400 includes a base 410, a rotatable wheel 420, a clamp 430, a stationary hub 440, and a tension adjustment 450. Base 410 is affixed to, or integral with, stationary hub 440. Clamp 430 is releasably affixed to rotatable wheel 420. Rotatable wheel 420 is rotatably engaged with stationary hub 440. Tension adjustment 450 is coupled with stationary hub 440 or base 410, and/or rotatable wheel 420.

In some embodiments, base 410 is a padded or cushioned element that is configured to comfortably abut the patient's abdominal/pelvic body wall 12 when penile traction device 400 is in use. Base 410 may be made of molded plastic, formed metal, laminated metal or plastic, and any other suitable materials and combinations of materials. In some embodiments, one or more surface cushioning members are included on base 410. Such cushioning may be made of materials such as, but not limited to, foam rubber, silicone, nitrile, polyurethane, latex, and the like. In some embodiments, the cushioning is configured as one or more pads, and the pads are removable/replaceable.

In the depicted embodiment, base 410 is affixed to, or integral with, stationary hub 440. For example, in some embodiments base 410 is attached to stationary hub 440 using mechanical fasteners such as, but not limited to, screws, pins, rivets, and the like. In some embodiments, base 410 is attached to stationary hub 440 by welding or using adhesive. In some embodiments, a combinations of affixing means are used. In particular embodiments, base 410 is made integrally with stationary hub 440. That is, base 410 and stationary hub 440, together, can be a single component part in some embodiments.

Rotatable wheel 420 is rotatably engaged with stationary hub 440. That is, rotatable wheel 420 can be rotated in relation to stationary hub 440. For example, as viewed in FIG. 5, rotatable wheel 420 can be rotated clockwise in relation to stationary hub 440 to increase tensile forces on penis 10, and/or rotated counter-clockwise in relation to stationary hub 440 to decrease tensile forces on penis 10. While in the depicted embodiment, rotatable wheel 420 is a full 360° member, in some embodiments rotatable wheel 420 is a circular segment or arcuate segment defining an arc of less than a full 360°.

While in the depicted embodiment the outer periphery of rotatable wheel 420 is essential circular, in some embodiments other shapes are defined by the outer surface of rotatable wheel 420, or by a portion of rotatable wheel 420. For example, the outer surface of rotatable wheel 420, or a portion thereof, may define a shape that includes two or more different radii, is partially linear, and the like, and combinations thereof.

In some embodiments, rotatable wheel 420 is a segmented member. That is, in some embodiments rotatable wheel 420 is comprised of two or more segments that are movable relative to each other (e.g., like the links of a tank track).

In some embodiments, penile traction device 400 includes a ratcheting mechanism that maintains a desired relative position between rotatable wheel 420 and stationary hub 440. For example, in some embodiments a desired amount of tensile force to penis 10 can be applied and maintained (i.e., releasably locked) using such a ratcheting mechanism. The ratcheting mechanism can be releasable and/or reversible in some embodiments. In some embodiments, other types of releasable locking mechanisms can be included. For example, clamping devices, detents, latches, spring mechanisms, elastic members, and the like, and combinations thereof, can be used to attain and releasably maintain a desired relative position between rotatable wheel 420 and stationary hub 440.

In the depicted embodiment, penile traction device 400 includes tension adjustment 450. Tension adjustment 450 is an adjustment mechanism for increasing or decreasing amount of tension applied to penis 10. In some embodiments, tension adjustment 450 is used to adjust a relative position of rotatable wheel 420 in relation to stationary hub 440. In some such embodiments, tension adjustment 450 is affixed to rotatable wheel 420 such that rotating tension adjustment 450 causes a rotation of rotatable wheel 420 in relation to stationary hub 440. In some such embodiments, tension adjustment 450 is used to adjust an amount of force applied to rotatable wheel 420 in relation to stationary hub 440. For example, tension adjustment 450 may be used to wind or unwind a torsion spring that applies a force to rotatable wheel 420 in relation to stationary hub 440 (thereby applying tension to penis 10, or releasing tension from penis 10).

In some embodiments, penile traction device 400 is configured with one or more indicator mechanisms that can detect and/or provide an indication of an amount of applied tension and/or penile length. For example, in particular embodiments graduations and/or numerical markings may be present on either one of, or both of, rotatable wheel 420 and stationary hub 440. Such graduations and/or numerical markings may provide an indication of penile length and may be useful for charting the progress of the treatment provided by penile traction device 400. In some embodiments, a tension indicator mechanism can be included. Such tension indicator mechanisms can be analog or digital. For example, a spring-based analog tension measurement device, an electronic strain gauge device, and other types of devices for measuring force/tension can be included so that a measureable and known amount of tension can be applied to penis 10.

In the depicted embodiment, the outer peripheral surface of rotatable wheel 420 is concaved (e.g., like a pulley) to comfortably receive penis 10 therein. In some embodiments, the concavity of the outer peripheral surface of rotatable wheel 420 may be adjustable. In some embodiments, rotatable wheels 420 of different concavity sizes may be interchangeable such that penile traction device 400 can be customized for a particular patient-user. In various embodiments, the surface (or portions thereof) that are configured for contact with penis 10 may be padded or cushioned. Such cushioning may be made of materials such as, but not limited to, foam rubber, silicone, nitrile, polyurethane, latex, and the like. In some embodiments, the cushioning is configured as one or more pads, and the pads are removable/replaceable.

Penile traction device 400 also includes clamp 430. Clamp 430 is used to couple penis 10 to rotatable wheel 420.

In the depicted embodiment, clamp 430 is releasably affixed to rotatable wheel 420. For example, in some embodiments clamp 430 is hinged in relation to rotatable wheel 420. In some such embodiments, clamp 430 is releasably detainable in various positions in relation to rotatable wheel 420 so as to provide a clamping force that can accommodate various sizes of penis 10. As with the concaved periphery of rotatable wheel 420, the surface of clamp 430 that contacts penis 10 can be concave, and may be padded or cushioned for patient-user comfort.

Figure 7:
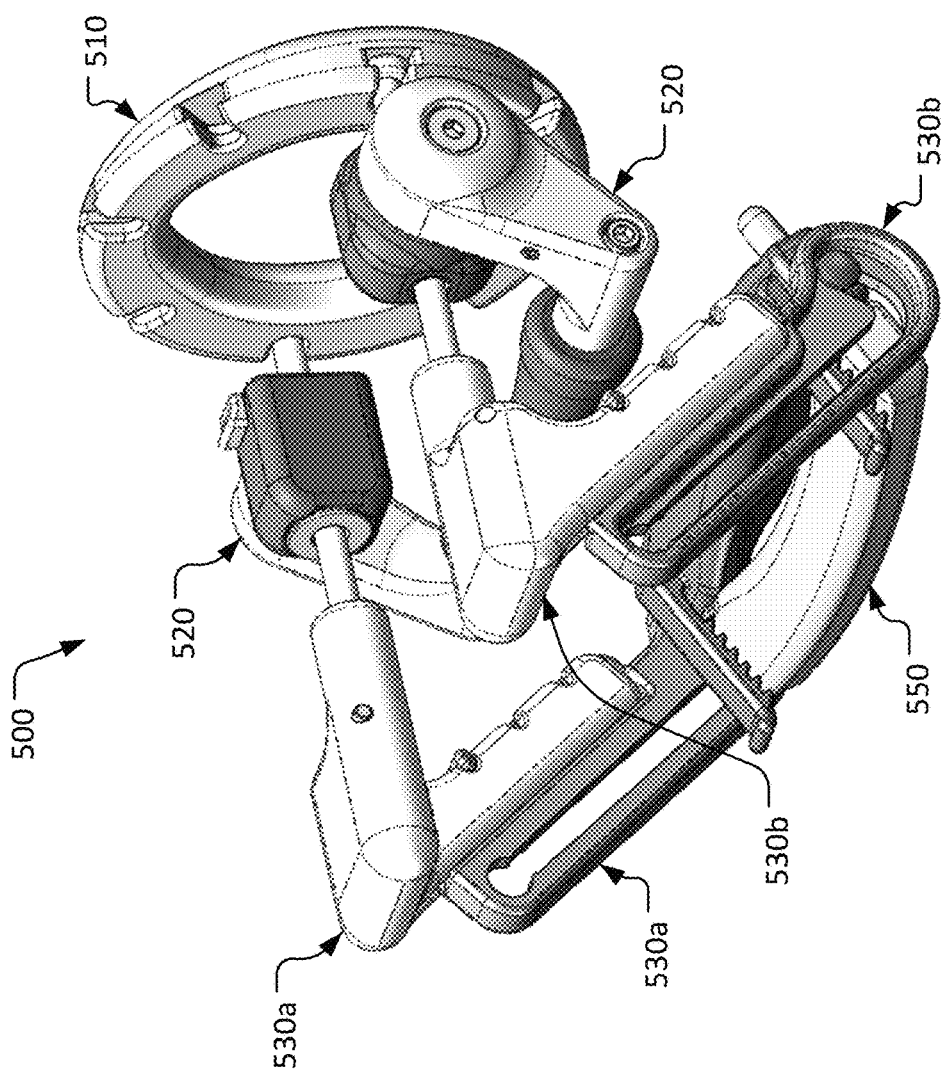
FIG. 7 is a perspective view of another example penile traction device in accordance with some embodiments provided herein.

Referring to FIG. 7, another example penile traction device 500 can be used to treat a human penis in accordance with the treatments and usages described above. Such treatments may be related to, but are not necessarily exclusively related to, Peyronie's disease. In some implementations, the treatments may be, but are not limited to, increasing penile length and/or correcting penile curvature. Penile traction device 500 is configurable to be well-suited to apply tensile traction forces to thereby provide penile length enhancement treatments. In some embodiments, penile traction device 500 is configured so that it can be discreetly worn under the clothes of a patient-user.

As described further below, each particular penile traction device 500 is adjustable so that a range of sizes can be treated by a particular size of penile traction device 500. For example, penile traction device 500 can adjusted within a range of sizes such that a patient-user may start with penile traction device 500 configured to have a first size and later progress to one or more larger sizes. Moreover, the design of penile traction device 500 is scalable to a variety of different sizes. For example, penile traction device 500 can be made in a range of sizes such that a patient-user may start with a first device 500, and then progress to a larger size device 500. All such sizes are within the scope of this disclosure.

In the depicted embodiment, penile traction device 500 includes a base 510, a tensioner subassembly 520, angle arm subassemblies 530a and 530b, and a clamp 550. Particular components and subassemblies of penile traction device 500 are adjustably coupled to each other as described further below.

Figure 8:
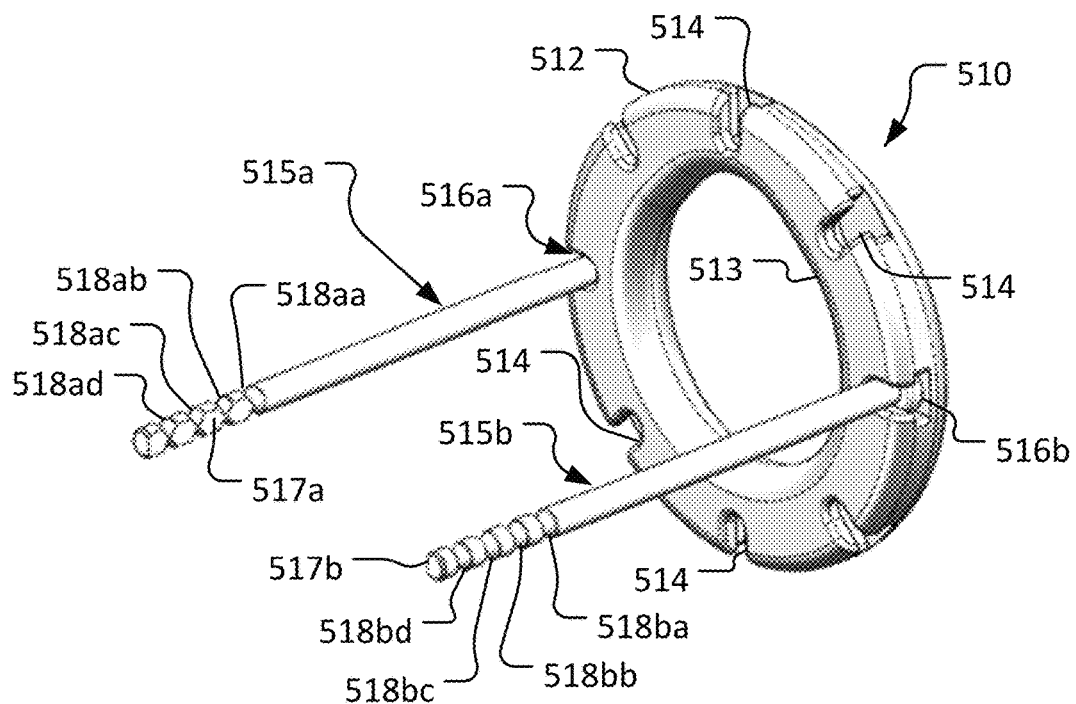
FIG. 8 is a perspective view of a subassembly of the penile traction device of FIG. 7.

Referring to FIG. 8, base 510 includes a pelvic interface member 512, a first extension rod 515a, and a second extension rod 515b. First and second extension rods 515a and 515b are selectively coupleable with pelvic interface member 512.

Pelvic interface member 512 is configured to press against the male abdomen when penile traction device 500 is being used. Pelvic interface member 512 may be made of, for example, any of the plastics or metals listed above in reference to frame members 112. In addition, in some embodiments surface padding or cushioning is included on the side that contacts the male body. Such cushioning may be made of materials such as, but not limited to, foam rubber, silicone, nitrile, polyurethane, latex, and the like. In some embodiments, the cushioning is configured as one or more pads, and the pads are removable/replaceable. In some embodiments, the surface of pelvic interface member 512 that presses against the abdomen is planar. In some embodiments, the surface of pelvic interface member 512 that presses against the abdomen is contoured with a curvature, or compound curvatures. In some embodiments, pelvic interface member 512 is malleable so that it can be custom-conformed to the shape of the user's abdomen.

Pelvic interface member 512 defines a clearance area 513 through which a penis to be treated by penile traction device 500 can extend. Clearance area 513 can be various shapes such as circular, ovular, egg-shaped, triangular, and the like.

Pelvic interface member 512 also defines T-slots 514. Two or more T-slots 514 may be defined by pelvic interface member 512. In some embodiments, two, four, six, eight, ten, or more than ten T-slots 514 are defined by pelvic interface member 512. In the depicted embodiment, eight T-slots 514 are defined by pelvic interface member 512. T-slots 514 have T-shaped cross-sectional shapes that are configured to releasably mate with complementarily-shaped proximal ends of first and second extension rods 515a and 515b as shown.

Base 510 also includes first and second extension rods 515a and 515b. First and second extension rods 515a and 515b can be made of any suitable polymeric or metallic material, and combinations of materials. First and second extension rods 515a and 515b can be available in various lengths. Appropriate lengths of first and second extension rods 515a and 515b can be selected for a particular penile size. In some embodiments, a kit with multiple sizes of first and second extension rods 515a and 515b can be provided (e.g., refer to FIG. 27). The extension rods 515a and 515b may also be linear or nonlinear, such that, after interfacing with base 510, the direction may be applied downward to the remainder of the assembly.

First and second extension rods 515a and 515b have first and second proximal ends 516a and 516b, respectively. (First proximal end 516a is obscured from view in FIG. 8.) First and second proximal ends 516a and 516b are shaped to releasably mate with T-slots 514. First and second extension rods 515a and 515b can be coupled with any T-slot 514 as desired. Because pelvic interface member 512 defines multiple T-slots 514, any two particular T-slots 514 that are in 180° opposition to each other can be selected for coupling with first and second extension rods 515a and 515b. Two particular T-slots 514 can be selected so that positioning first and second extension rods 515a and 515b therein will induce a bend to the penis that is counter to the disease-state angle of the penis.

First and second extension rods 515a and 515b have distal ends with flats 517a and 517b respectively. The purpose of flats 517a and 517b will be described further below.

In the depicted embodiment, the distal ends of first and second extension rods 515a and 515b include multiple annular grooves. That is, first extension rod 515a includes annular grooves 518aa, 518ab, 518ac, and 518ad. Similarly, second extension rod 515b includes annular grooves 518ba, 518bb, 518bc, and 518bd. Such multiple annular grooves provide adjustability of penile traction device 500, as described further below. While in the depicted embodiment, each extension rod 515a and 515b includes four annular grooves, in some embodiments one, two, three, four, five, six, seven, eight, or more than eight annular grooves are included in each extension rod 515a and 515b.

Figure 9:
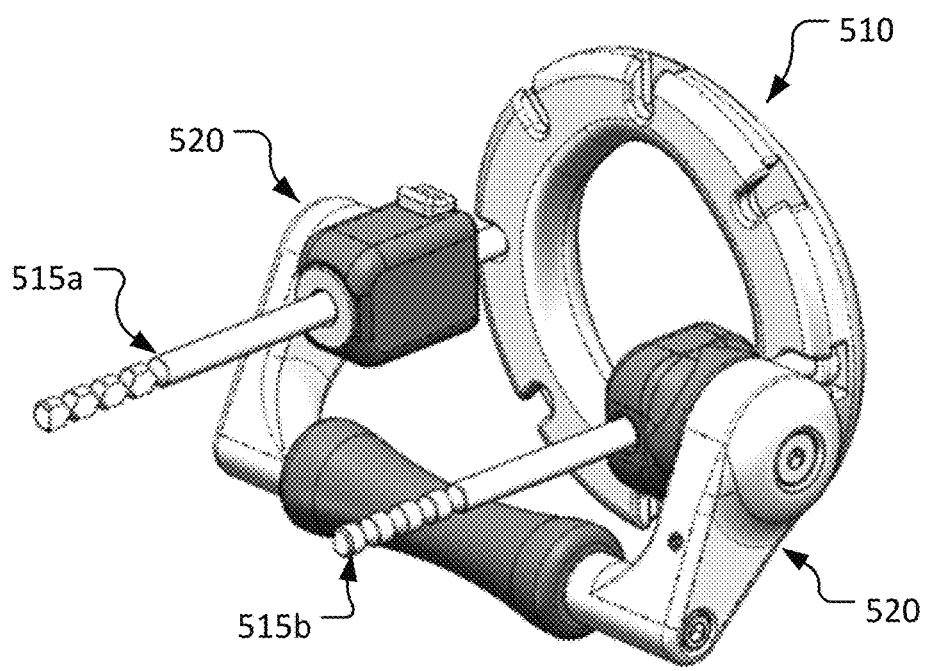
FIG. 9 is a perspective view of another subassembly of the penile traction device of FIG. 7.

Referring to FIG. 9, penile traction device 500 also includes tensioner subassembly 520. Tensioner subassembly 520 is slidably engaged with base 510. In particular, tensioner subassembly 520 is slidable engaged with first and second extension rods 515a and 515b. As described further below, tensioner subassembly 520 is selectively lockable on first and second extension rods 515a and 515b. That is, tensioner subassembly 520 can be releasably locked at various positions along the lengths of first and second extension rods 515a and 515b. In that manner, penile traction device 500 is adjustable to accommodate various anatomical sizes and various treatment parameters.

Referring also to FIGS. 10A-10C, tensioner subassembly 520 includes a torsion-spring rod receiver 522a, a linear-locking rod receiver 522b, a first tensioner arm 526a, a second tensioner arm 526b, and a force-application member assembly 528. In the depicted embodiment, torsion-spring rod receiver 522a is slidably coupleable with first extension rod 515a, and linear-locking rod receiver 522b is slidably coupleable with second extension rod 515b. In some embodiments, torsion-spring rod receiver 522a can be slidably coupleable with second extension rod 515b, and linear-locking rod receiver 522b can be slidably coupleable with second extension rod 515b.

First tensioner arm 526a is pivotably coupled to torsion-spring rod receiver 522a, and second tensioner arm 526b is pivotably coupled to linear-locking rod receiver 522b. Force-application member assembly 528 extends between first tensioner arm 526a and second tensioner arm 526b.

Torsion-spring rod receiver 522a includes a torsion spring 523 and a spring-force adjustment mechanism 524. As described further below, torsion spring 523 provides a springy force (via force-application member assembly 528) for bending and/or extending a penis receiving treatment by penile traction device 500. The force applied by torsion spring 523 can be adjusted using spring-force adjustment mechanism 524. In the depicted embodiment, spring-force adjustment mechanism 524 is a setscrew that is threadably adjustable to apply various amounts of preload to torsion spring 523.

Linear-locking rod receiver 522b includes a rod-locking mechanism 525. Rod-locking mechanism 525 allows the linear-locking rod receiver 522b (and the tensioner subassembly 520 as a whole) to be locked to first extension rod 515a, and to be unlocked so that linear-locking rod receiver 522b (and the tensioner subassembly 520 as a whole) can be slid along first extension rod 515a. Rod-locking mechanism 525 is biased to being locked to first extension rod 515a. That is, the unactuated state of rod-locking mechanism 525 locks linear-locking rod receiver 522b (and the tensioner subassembly 520 as a whole) to first extension rod 515a. In contrast, to slide linear-locking rod receiver 522b (and the tensioner subassembly 520 as a whole) along first extension rod 515a, rod-locking mechanism 525 needs to be physically actuated to unlock linear-locking rod receiver 522b from first extension rod 515a.

First tensioner arm 526a is pivotably coupled to torsion-spring rod receiver 522a, and second tensioner arm 526b is pivotably coupled to linear-locking rod receiver 522b. As described further below, torsion spring 523 biases tensioner arms 526a and 526b to positioned in a particular configuration in relation to torsion-spring rod receiver 522a and linear-locking rod receiver 522b.

Force-application member assembly 528 extends between first tensioner arm 526a and second tensioner arm 526b. In the depicted embodiment, lateral traction force-application member assembly 528 includes a cambered roller 529 that can turn on its longitudinal axis (e.g., in relation to tensioner arms 526a and 526b). In some embodiments, cambered roller 529 is made of a smooth, compliant, lubricious material. For example, in some embodiments cambered roller 529 is made of materials such as, but not limited to, foam rubber, silicone, nitrile, polyurethane, latex, and the like.

Figure 11A:
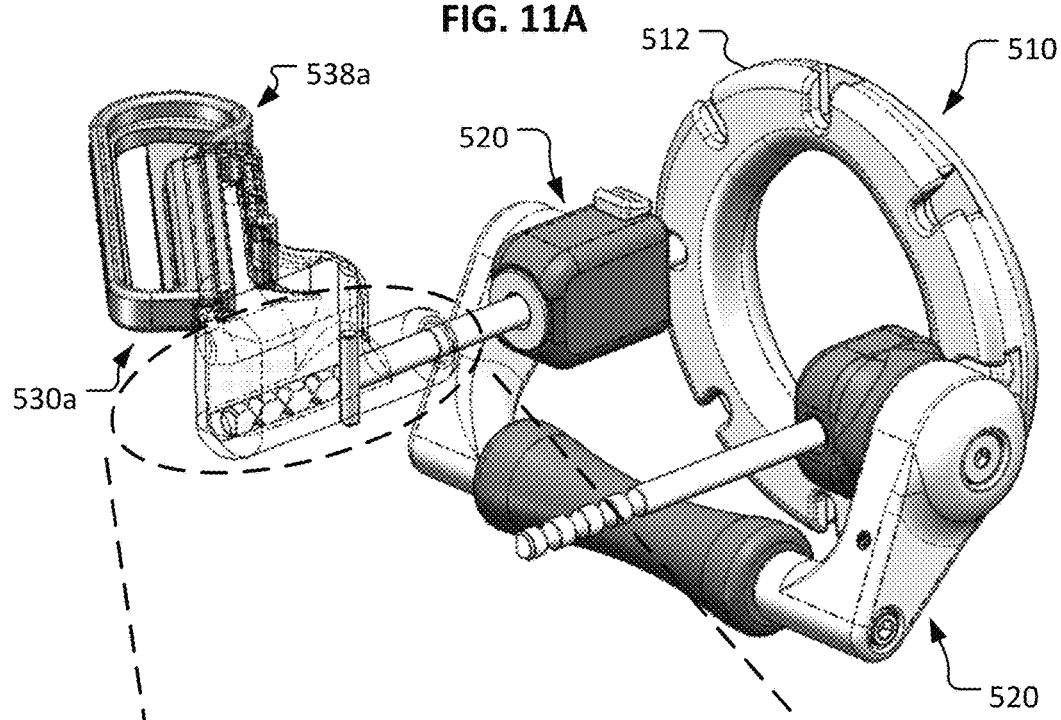
FIG. 11A is a perspective view of another subassembly of the penile traction device of FIG. 7.
Figure 11B:
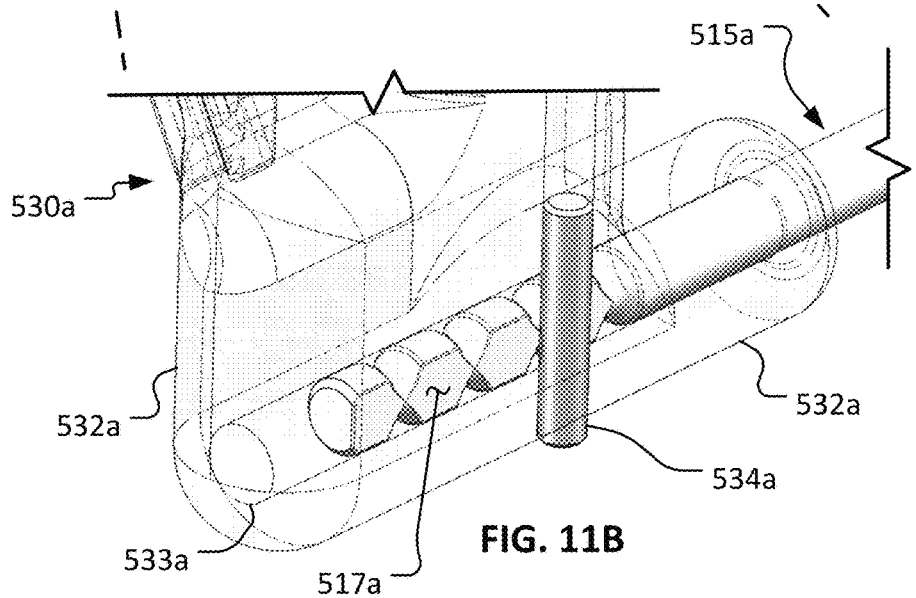
FIG. 11B is a transparent perspective view of a portion of the subassembly of FIG. 11A.

Referring to FIGS. 11A and 11B, angle arm subassembly 530a is adjustably coupleable to first extension rod 515a. Angle arm subassembly 530a includes angle arm 532a, angle arm pin 534a, and clamp track 538a. Angle arm pin 534a is affixed to angle arm 532a. Clamp track 538a is adjustably coupleable to angle arm 532a.

These figures illustrate how angle arm 530a can be coupled with, and positionally adjusted in relation to, first extension rod 515a. Angle arm 532a is shown transparently so that the coupling mechanisms between angle arm 530a and first extension rod 515a can be visualized. Angle arm 530b (FIG. 7) can be adjustably coupled to second extension rod 515b in the same manner.

Figure 12A:
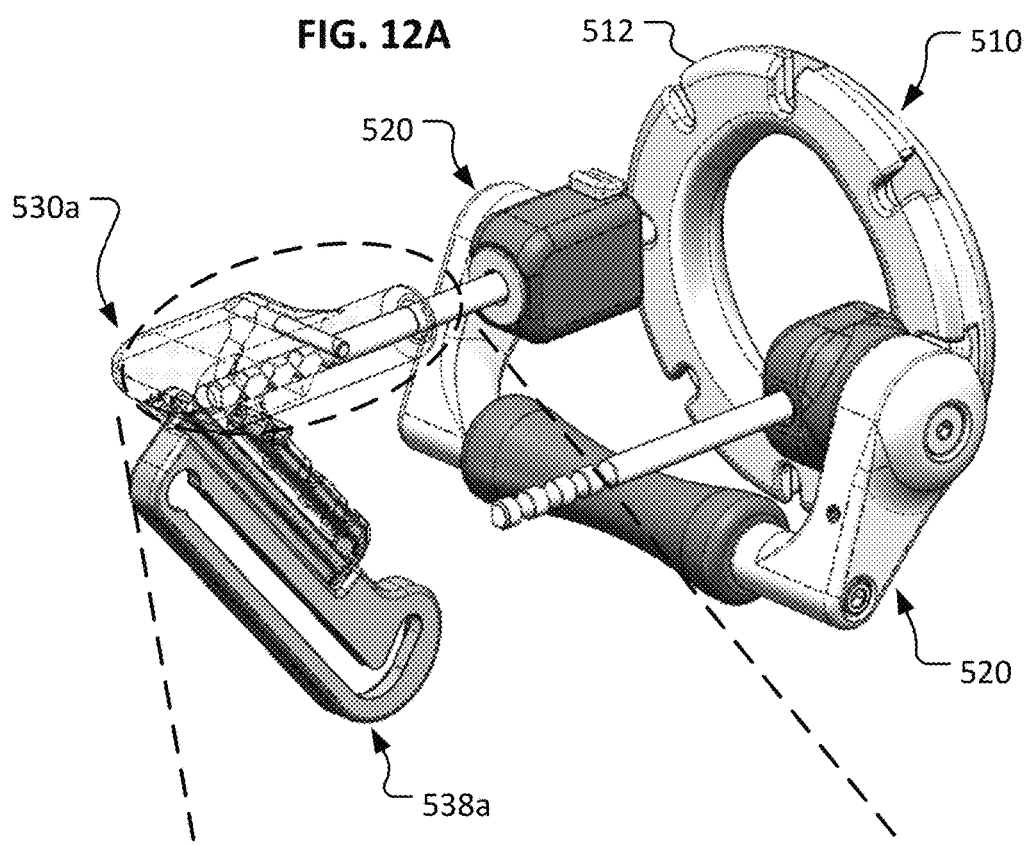
FIG. 12A is a perspective view of another subassembly of the penile traction device of FIG. 7.
Figure 12B:
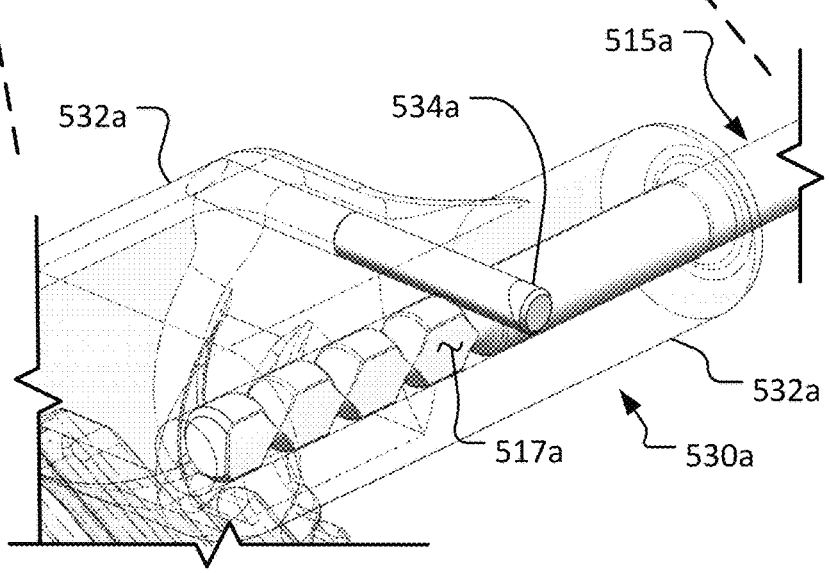
FIG. 12B is a transparent perspective view of a portion of the subassembly of FIG. 12A.

Angle arm 532a defines a bore 533a that can slidably receive a distal end portion of first extension rod 515a. While bore 533a is generally cylindrical, angle arm pin 534a partially intersects bore 533a (in a transverse direction to the longitudinal axis of bore 533a). Consequently, as angle arm 532a is slid onto first extension rod 515a, angle arm pin 534a will physically interfere with first extension rod 515a unless angle arm 532a is oriented so that the protrusion of angle arm pin 534a in bore 533a is aligned with flat 517a. Said differently, when the longitudinal axis of angle arm pin 534a is parallel with the plane defined by flat 517a (as shown in FIGS. 11A and 11B), angle arm 532a can be freely slid onto first extension rod 515a. It is also true that, when the longitudinal axis of angle arm pin 534a is unparallel with the plane defined by flat 517a (e.g., as shown in FIGS. 12A and 12B), angle arm 532a cannot be freely slid along first extension rod 515a.

Angle arm pin 534a is releasably coupleable with any one of annular grooves 518aa, 518ab, 518ac, and 518ad (FIG. 8). That is, annular grooves 518aa, 518ab, 518ac, and 518ad are sized for a close slip fit with the portion of angle arm pin 534a that protrudes in bore 533a.

The fact that angle arm pin 534a is releasably coupleable with any one of annular grooves 518aa, 518ab, 518ac, and 518ad provides adjustability of penile traction device 500. For example, when angle arm pin 534a is coupled with annular groove 518aa, angle arm subassembly 530a is positioned closer to pelvic interface member 512 than when angle arm pin 534a is coupled with annular grooves 518ab, 518ac, or 518ad. It is also true that when angle arm pin 534a is coupled with annular groove 518ad, angle arm subassembly 530a is positioned farther away from pelvic interface member 512 than when angle arm pin 534a is coupled with annular grooves 518aa, 518ab, or 518ac.

As described above, angle arm subassembly 530a can be slid onto first extension rod 515a when the longitudinal axis of angle arm pin 534 is parallel with the plane defined by flat 517a. Then, with angle arm subassembly 530a on first extension rod 515a such that angle arm pin 534a is aligned with any one of annular grooves 518aa, 518ab, 518ac, and 518ad, angle arm subassembly 530a can be pivoted about the longitudinal axis of first extension rod 515a to releasably couple angle arm subassembly 530a to first extension rod 515a.

Referring to FIGS. 12A and 12B, as described above, angle arm subassembly 530a is pivotable about the longitudinal axis of first extension rod 515a to releasably couple angle arm subassembly 530a to first extension rod 515a. Angle arm 530b (FIG. 7) can be adjustably coupled to second extension rod 515b in the same manner.

Extension rods 515a and 515b and angle arm subassemblies 530a and 530b together comprise a frame of penile traction device 500 that extends from the base 510.

Figure 13:
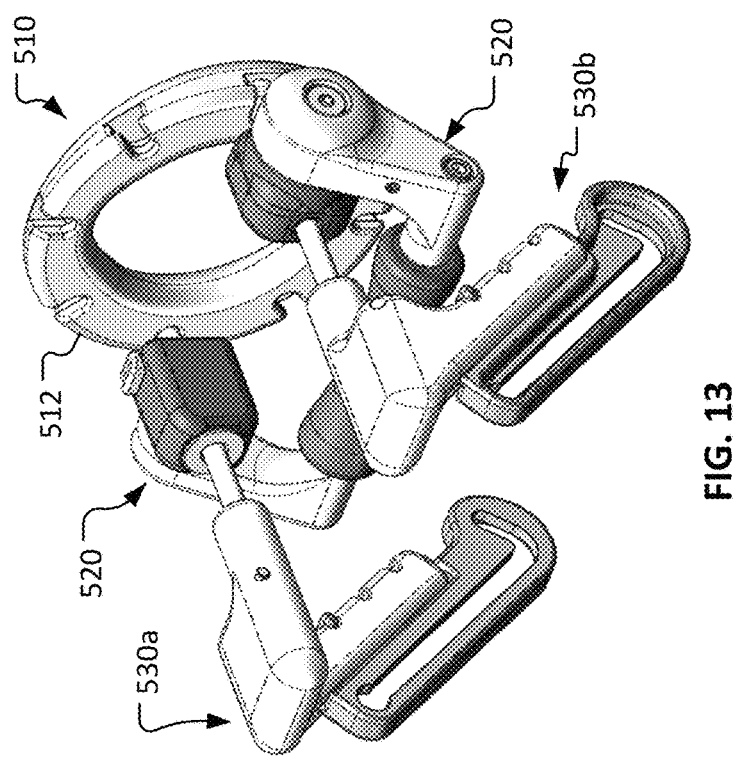
FIG. 13 is a perspective view of another subassembly of the penile traction device of FIG. 7.

Referring to FIG. 13, both angle arm subassemblies 530a and 530b can be releasably coupled to base 510 in the aforementioned manner. It should be understood that the positions of angle arm subassemblies 530a and 530b in relation to pelvic interface member 512 can be adjusted by pivoting angle arm subassemblies 530a and 530b to the orientation of FIGS. 11A and 11B, and then sliding angle arm subassemblies 530a and 530b proximally or distally in relation to base 510.

Figure 14:
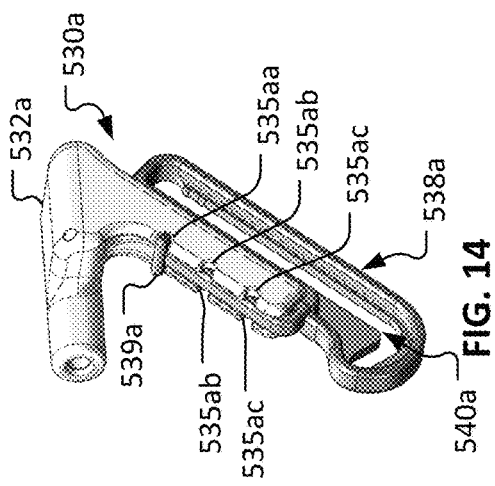
FIG. 14 is a perspective view of another subassembly in a first configuration of the penile traction device of FIG. 7.
Figure 15:
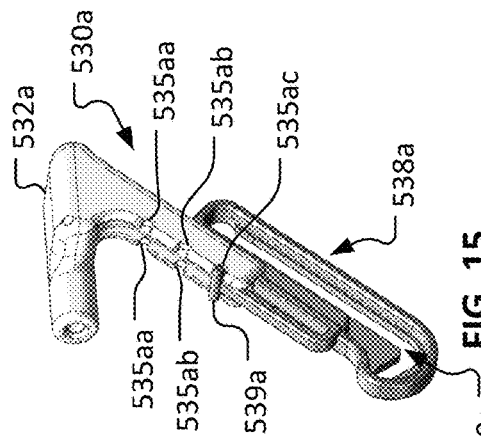
FIG. 15 is a perspective view of the subassembly of FIG. 15 in a second configuration.

Referring also to FIGS. 14 and 15, clamp track 538a is adjustably coupled with angle arm 532a to comprise angle arm subassembly 530a, and the analogous arrangement comprises angle arm subassembly 530b.

Clamp track 538a includes an engagement pin 539a. Angle arm 532a defines one or more grooves 535aa, 535ab, and 535ac that are configured to releasably receive engagement pin 539a. In the depicted embodiment, three grooves 535aa, 535ab, and 535ac are defined by angle arm 532a. In some embodiments, one, two, three, four, five, six, or more than six such grooves may be defined by angle arm 532a.

When engagement pin 539a is positioned within one of the grooves 535aa, 535ab, and 535ac, clamp track 538a is releasably coupled with angle arm 532a. The fact that engagement pin 539a is releasably coupleable with any one of grooves 535aa, 535ab, and 535ac provides adjustability of penile traction device 500. For example, when engagement pin 539a is coupled with groove 535aa (as shown in FIG. 14), clamp track 538a and angle arm 532a comprise a shorter angle arm subassembly 530a than when engagement pin 539a is coupled with grooves 535ab or 535ac. It is also true that when engagement pin 539a is coupled with groove 535ac (as shown in FIG. 15), clamp track 538a and angle arm 532a comprise a longer angle arm subassembly 530a than when engagement pin 539a is coupled with grooves 535aa or 535ab. The length of angle arm subassembly 530b can be adjusted in the same way.

Clamp track 538a defines an angle arm track 540a. In the depicted embodiment, angle arm track 540a is a slot that is configured to slidably couple clamp 550 (FIG. 7) to angle arm subassembly 530a.

Figure 17:
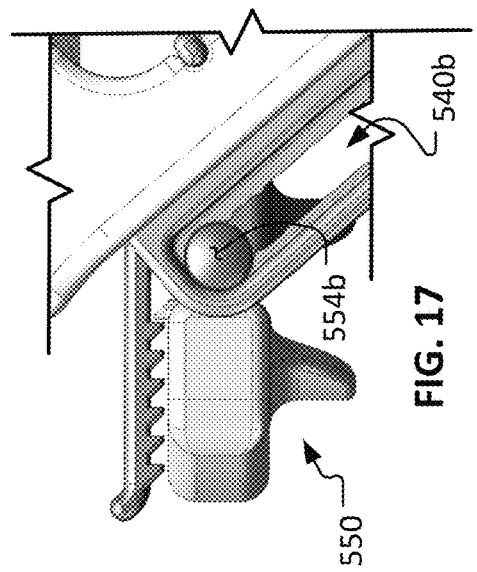
FIG. 17 is a side view of a portion in a first configuration of the penile traction device of FIG. 16.
Figure 18:
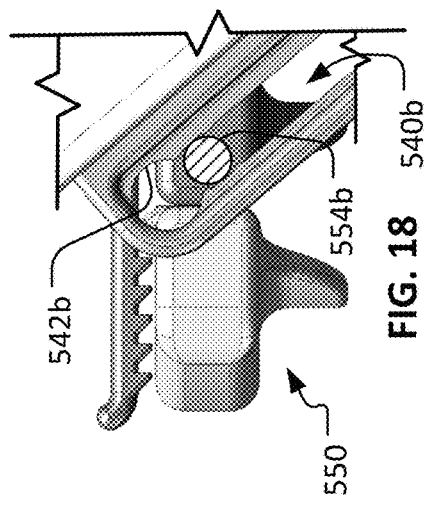
FIG. 18 is a side view of a portion in a second configuration of the penile traction device of FIG. 16.
Figure 16:
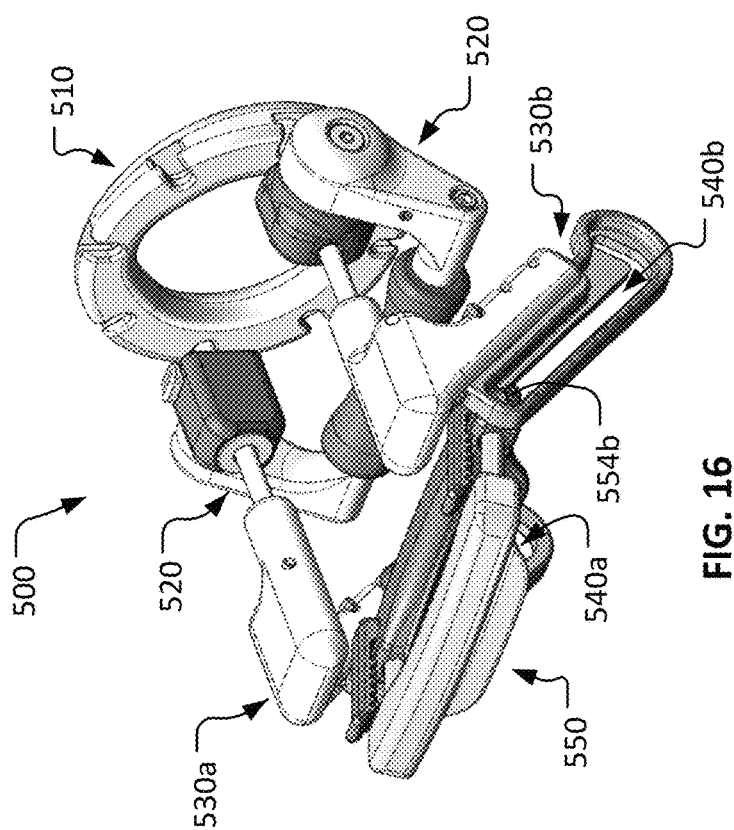
FIG. 16 is a perspective view of the penile traction device of FIG. 7 in another configuration.

Referring to FIGS. 16-18, clamp 550 can be slidably coupled to angle arm subassemblies 530a and 530b. Clamp 550 includes a first button head pivot pin 554a (obscured from view) and a second button head pivot pin 554b. First button head pivot pin 554a slidably couples with angle arm track 540a, and second button head pivot pin 554b slidably couples with an angle arm track 540b. Accordingly, when clamp 550 is coupled with angle arm subassemblies 530a and 530b, clamp 550 can be slid along the lengths of angle arm subassemblies 530a and 530b.

Angle arm track 540b includes an enlarged opening 542b (FIG. 18) defined at a first end of angle arm track 540b. Enlarged opening 542b is large enough such that clearance exists between the button head of second button head pivot pin 554b and enlarged opening 542b. The same relationship is present between first button head pivot pin 554a and the first end of angle arm track 540a. That is, the first end of angle arm track 540a includes an enlarged opening 542a (not visible). Enlarged opening 542a is large enough such that clearance exists between the button head of second button head pivot pin 554a and enlarged opening 542a. Accordingly, clamp 550 can be coupled to angle arm subassemblies 530a and 530b by passing button head pivot pins 554a and 554b through enlarged openings 542a and 542b respectively (e.g., as depicted in FIGS. 16 and 17).

With clamp 550 coupled to angle arm subassemblies 530a and 530b, clamp 550 can be slid along angle arm tracks 540a and 540b. Such sliding engagement is depicted in FIG. 18, in which the button head of second button head pivot pin 554b has been removed to provide enhanced visualization and understanding of the physical relationship between button head pivot pins 554a/554b and angle arm tracks 540a/540b respectively.

Referring to FIGS. 19-22, clamp 550 includes a first clamp half 552, a second clamp half 556, and elastomeric members 560a and 560b. Clamp 550 defines a clamp opening 551.

First clamp half 552 is slidable in relation to second clamp half 556, and is clampable with second clamp half 556. Elastomeric members 560a and 560b are arranged to prevent first clamp half 552 and second clamp half 556 from becoming detached from each other while first clamp half 552 and second clamp half 556 are unclamped from each other. In some embodiments, a single elastomeric member is included (rather than the two elastomeric members 560a and 560b).

Figure 20:
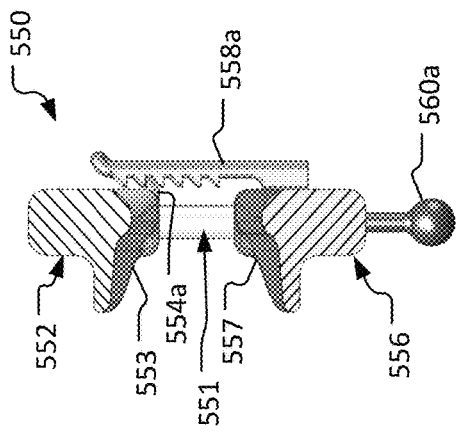
FIG. 20 is a cross-sectional side view of the clamp subassembly of FIG. 19.
Figure 19:
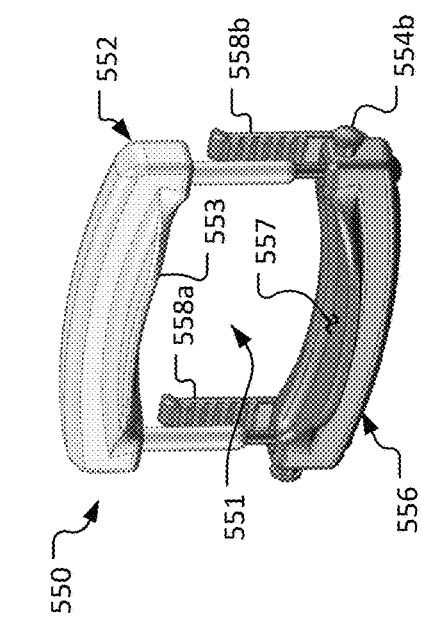
FIG. 19 is a perspective view of a clamp subassembly of the penile traction device of FIG. 17.
Figure 22:
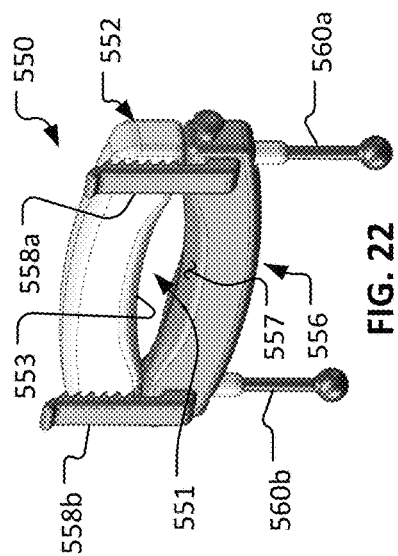
FIG. 22 is a perspective view of the clamp subassembly of FIG. 19 in a second clamped configuration.
Figure 21:
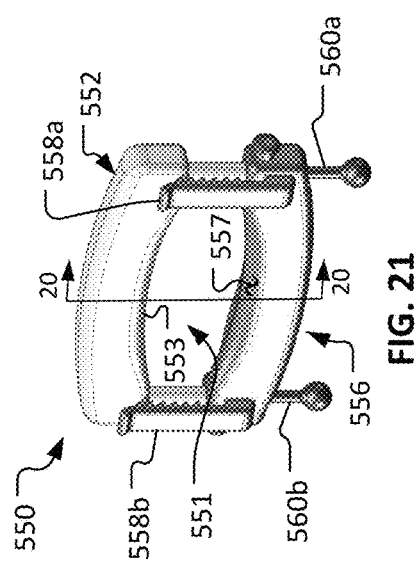
FIG. 21 is a perspective view of the clamp subassembly of FIG. 19 in a first clamped configuration.

FIG. 19 shows clamp 550 with first clamp half 552 and second clamp half 556 unclamped from each other (while still attached to each other via elastomeric members 560a and 560b). FIG. 20 shows a cross-sectional view of clamp 550 with first clamp half 552 and second clamp half 556 in a clamped configuration. FIG. 21 shows clamp 550 with first clamp half 552 and second clamp half 556 arranged in an upper clamping limit configuration (opening 551 is maximized while first clamp half 552 and second clamp half 556 are clamped together). FIG. 22 shows clamp 550 with first clamp half 552 and second clamp half 556 arranged in a lower clamping limit configuration (opening 551 is minimized while first clamp half 552 and second clamp half 556 are clamped together).

First clamp half 552 includes a first tooth 554a and a second tooth 554b (obscured from view). Second clamp half 556 includes a first tooth rack 558a and a second tooth rack 558b. First tooth 554a is arranged to mate anywhere along first tooth rack 558a, and second tooth 554b is arranged to mate anywhere along second tooth rack 558b. Hence, first clamp half 552 and second clamp half 556 can be clamped with each other so as to define different sizes of opening 551 (e.g., a large opening 551 in FIG. 21 and a small opening 551 in FIG. 22). To unclamp first clamp half 552 from second clamp half 556, first tooth rack 558a and second tooth rack 558b can be manually deflected away from first tooth 554a and second tooth 554b such that first tooth rack 558a becomes disengaged from first tooth 554a and second tooth rack 558b becomes disengaged from second tooth 554b.

While first clamp half 552 and second clamp half 556 are clamped with each other, a compressive clamping force can be delivered and maintained between a first clamp surface 553 and a second clamp surface 557. First clamp surface 553 and second clamp surface 557 can comprise materials and shapes that are comfortable for clamping. In some embodiments, clamp surfaces 553 and 557 are made of a smooth, compliant, lubricious material. For example, in some embodiments clamp surfaces 553 and 557 are made of materials such as, but not limited to, foam rubber, silicone, nitrile, polyurethane, latex, and the like. In some embodiments, clamp surfaces 553 and 557 are configured to have one or more pads. In some embodiments, such pad(s) is/are removable and replaceable. In some embodiments, such pad(s) is/are available in different materials, thicknesses, contours, textures, durometers, and other such properties to suit different uses, conditions, and anatomies. Moreover, in some embodiments, such as the depicted embodiment, clamp surfaces 553 and 557 include contoured "duckbill" surfaces to increase the contact area so that the compressive clamping force is distributed over a larger area (to reduce the clamping pressure and increase user-comfort).

FIGS. 23-26 are a series of figures illustrating the steps a user can perform to don and activate penile traction device 500.

Figure 23:
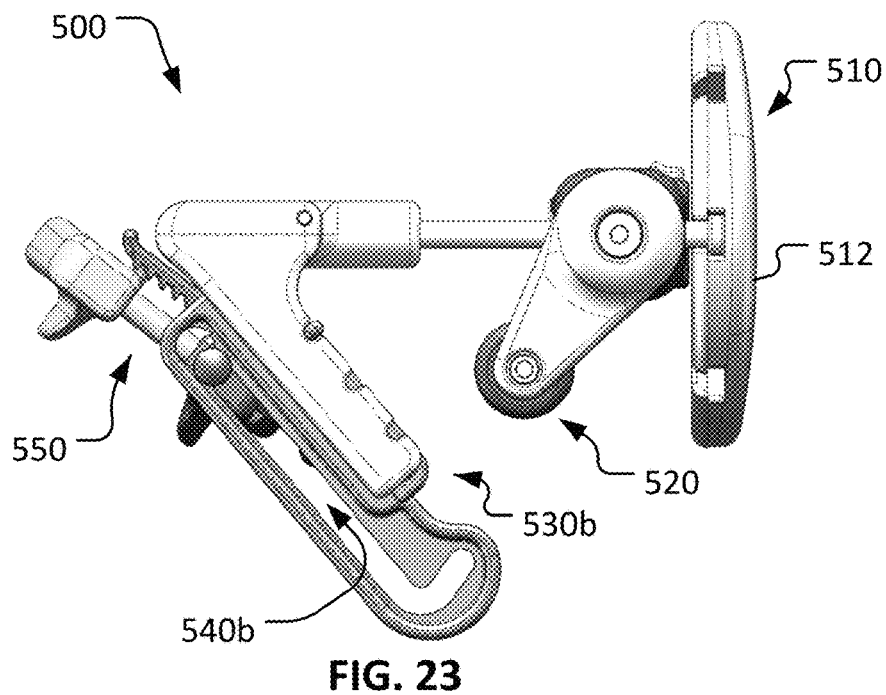
FIG. 23 is a side view of the penile traction device of FIG. 7 with the clamp subassembly in the first configuration.

Beginning with FIG. 23, penile traction device 500 is initially configured to be engaged with the user's anatomy. For example, tensioner subassembly 520 is slid near to pelvic interface member 512. Clamp 550 can be unclamped or in its maximum open configuration. Clamp 550 is slid near the first ends of angle arm tracks 540a (obscured from view) and 540b. Then, with penile traction device 500 in this arrangement, the user's penis can be extended through the openings of pelvic interface member 512 and clamp 550.

Figure 24:
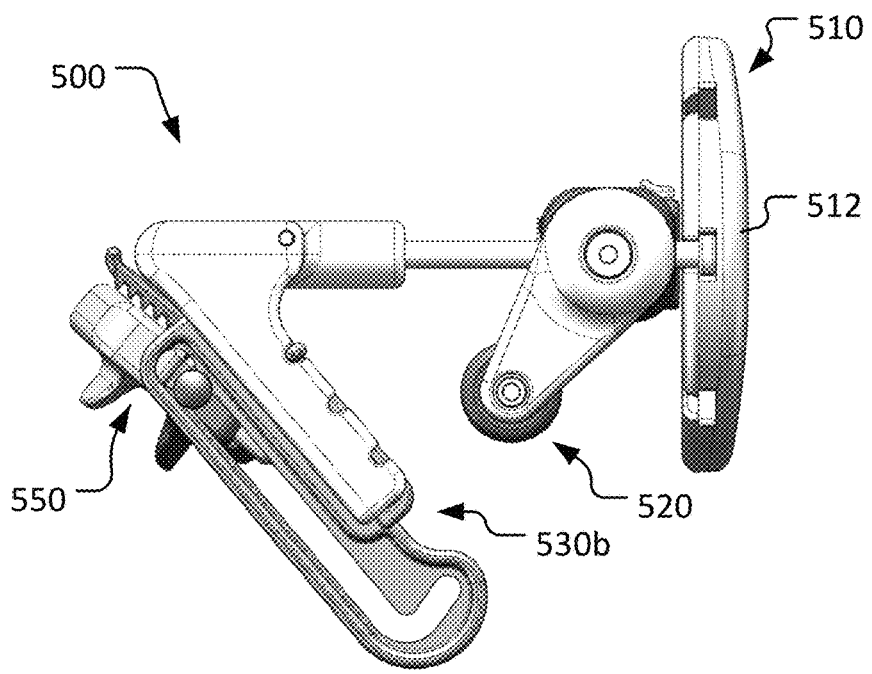
FIG. 24 is a side view of the penile traction device of FIG. 7 with the clamp subassembly in the second configuration.

As shown in FIG. 24, the next step is to gently compress an end portion of the user's penis within clamp 550. As the halves of clamp 550 are compressed towards each other, the teeth of the halves engage with each other (as described in reference to FIGS. 19-22) to maintain the clamped arrangement.

Figure 25:
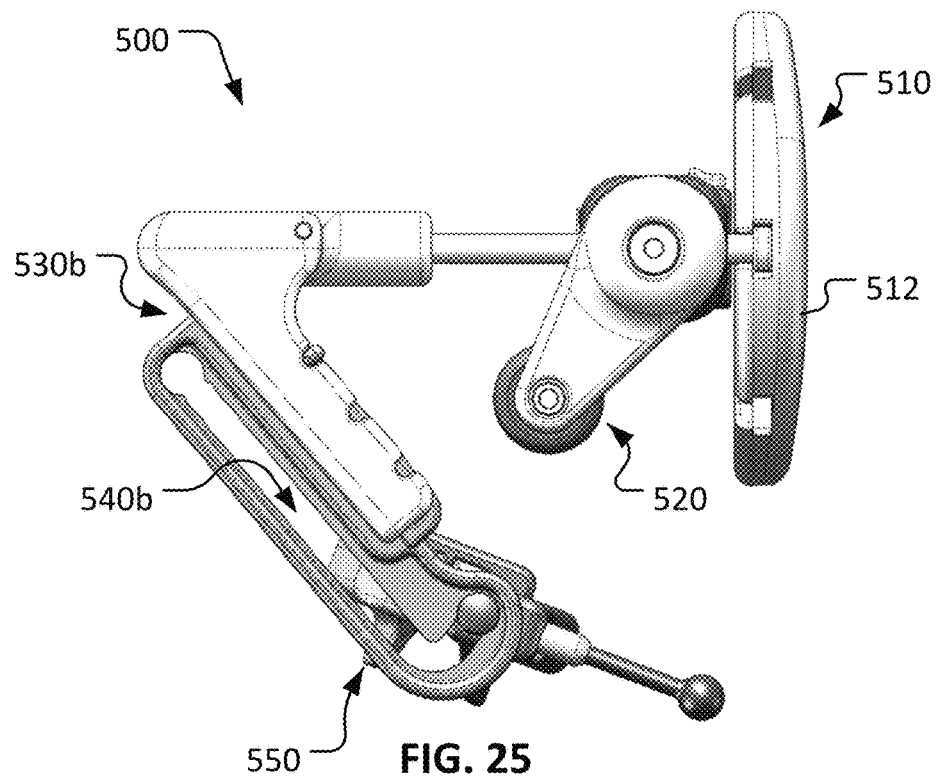
FIG. 25 is a side view of the penile traction device of FIG. 7 with the tensioner subassembly of FIG. 10A in a first configuration.

Next, as shown in FIG. 25, clamp 550 is manually slid towards a second end of angle arm tracks 540a and 540b. The second end of angle arm tracks 540a and 540b include a latching position that releasably retains clamp 550 at the second end of angle arm tracks 540a and 540b. In some cases, while clamp 550 is in this configuration, a slight tensile force is applied to the user's penis.

Figure 26:
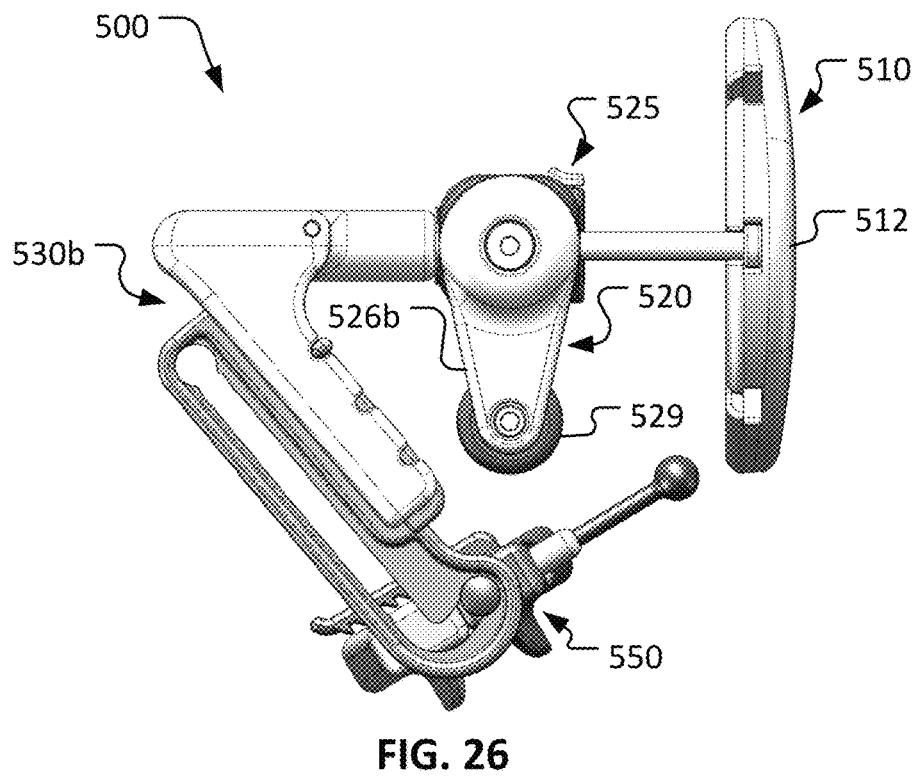
FIG. 26 is a side view of the penile traction device of FIG. 7 with the tensioner subassembly of FIG. 10A in a second configuration.

Lastly, as shown in FIG. 26, tensioner subassembly 520 is slid away (distally) from pelvic interface member 512. To slide tensioner subassembly 520, rod-locking mechanism 525 is first actuated. When tensioner subassembly 520 has been slid to the desired position, rod-locking mechanism 525 can be unactuated and then tensioner subassembly 520 remains locked in the desired position. This movement of tensioner subassembly 520 places force on the user's penis via cambered roller 529. In response to such force, tensioner arms 526a and 526b (FIG. 10A) will pivot and the loading on torsion spring 523 (FIG. 10B) will increase. Thereafter, torsion spring 523 will maintain the force(s) on the user's penis via cambered roller 529. Such force(s) provide the desired treatment (as described above).

Penile traction device 500 has the ability to attach penile traction device 500 onto the penis and then applying the tension load(s). The sliding tensioner subassembly 520 along with the attachment and tensioning positions of clamp 550 are features that provide this ability.

Figure 27:
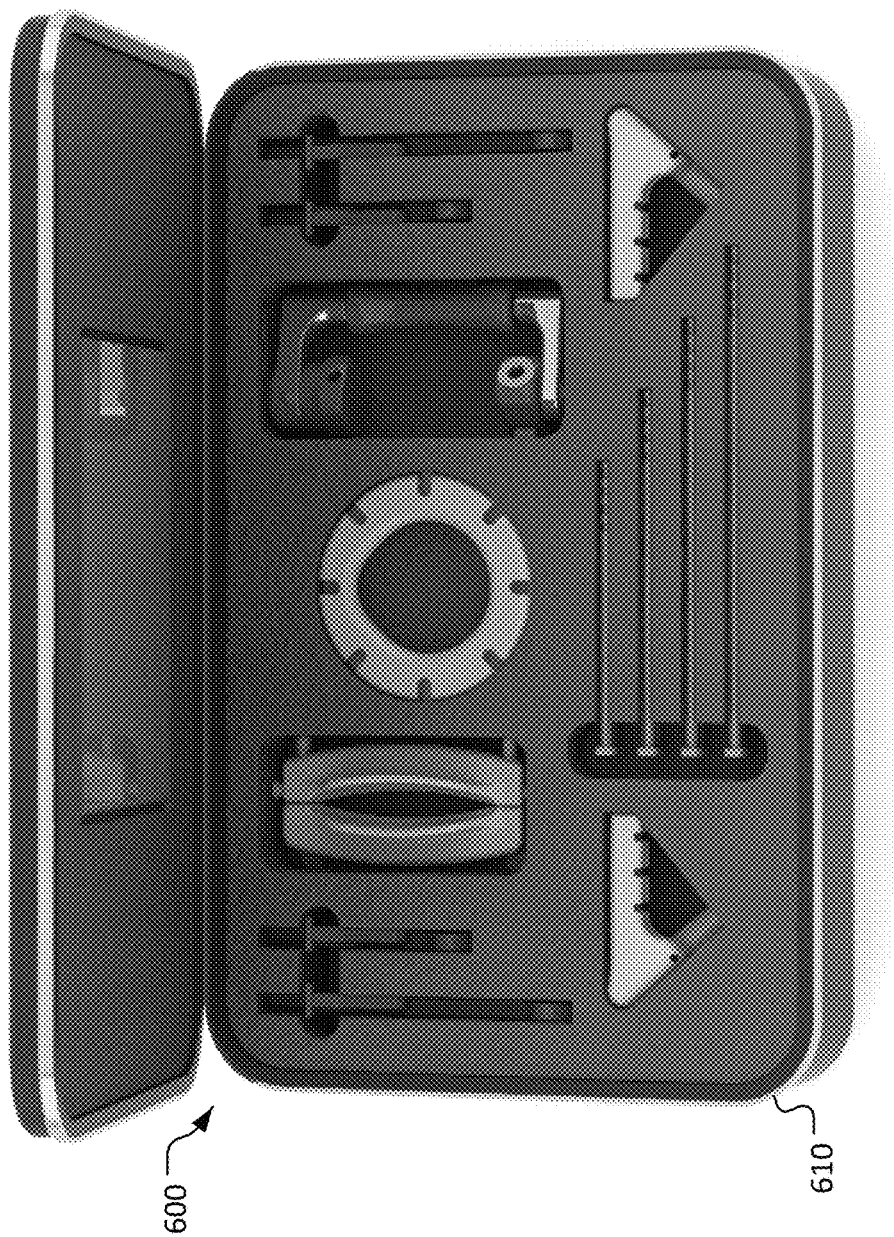
FIG. 27 is a top perspective view of a kit of components that can be assembled into the penile traction device of FIG. 7.

Referring to FIG. 27, a kit 600 can provide the components and subassemblies to assemble penile traction device 500. Kit 600 can include a case 610 that organizes the components and subassemblies to assemble penile traction device 500. Components and subassemblies of various sizes can be provided in kit 600. For example, extension rods of various lengths, and clamp tracks of various lengths can be provided in kit 600. In result, the fit of penile traction device 500 can be customized to a particular user, and can be adjusted for the particular user as the treatments progress.

Figure 28:
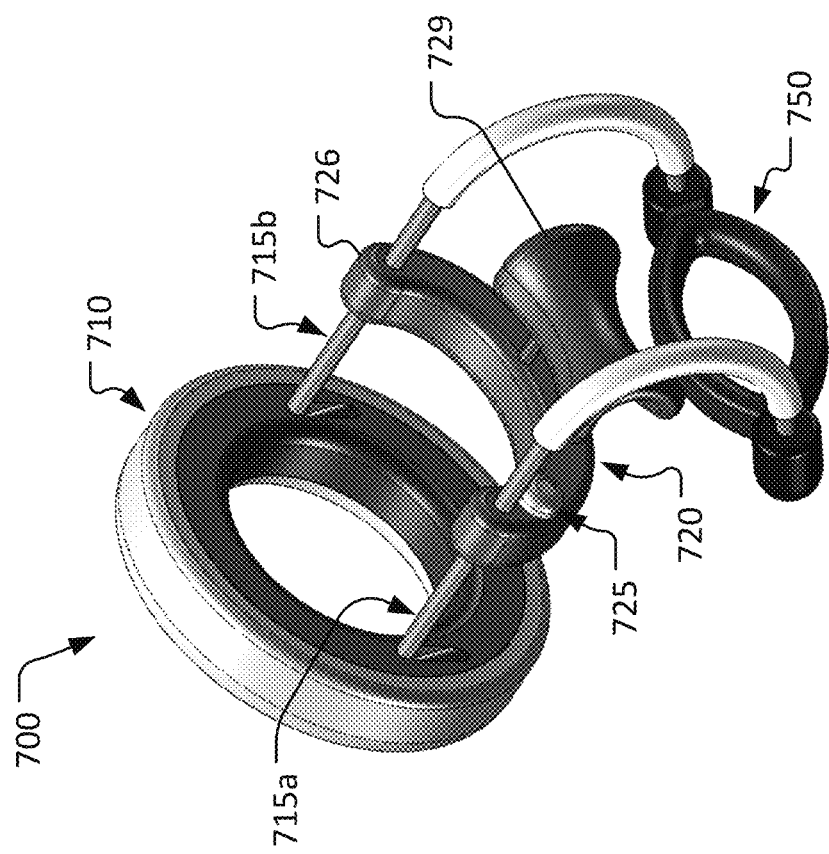
FIG. 28 is a perspective view of another example penile traction device in accordance with some embodiments provided herein.

Referring to FIG. 28, another example penile traction device 700 can be used to treat a human penis in accordance with the treatments and usages described above. Such treatments may be related to, but are not necessarily exclusively related to, Peyronie's disease. In some implementations, the treatments may be, but are not limited to, increasing penile length and/or correcting penile curvature. Penile traction device 700 is configurable to be well-suited to apply tensile traction forces to thereby provide penile length enhancement treatments. In some embodiments, penile traction device 700 is configured so that it can be discreetly worn under the clothes of a patient-user.

As described further below, each particular penile traction device 700 is adjustable so that a range of sizes can be treated by a particular size of penile traction device 700. For example, penile traction device 700 can adjusted within a range of sizes such that a patient-user may start with penile traction device 700 configured to have a first size and later progress to one or more larger sizes. Moreover, the design of penile traction device 700 is scalable to a variety of different sizes. For example, penile traction device 700 can be made in a range of sizes such that a patient-user may start with a first device 700, and then progress to a larger size device 700. All such sizes are within the scope of this disclosure.

In the depicted embodiment, penile traction device 700 includes a base 710, arms 715a and 715b, a tensioner subassembly 720, and a clamp 750. The components and subassemblies of penile traction device 700 are adjustably coupled to each other.

Arms 715a and 715b are pivotably coupled to base 710. Tensioner subassembly 720 is slidable on, and releasably lockable to, arms 715a and 715b. Clamp 750 is coupled to arms 715a and 715b.

Figure 29:
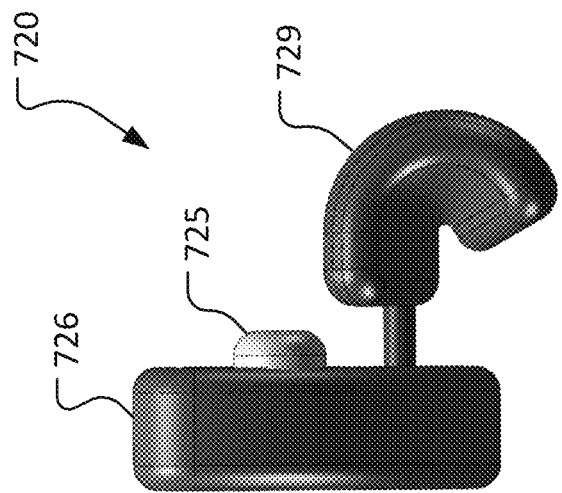
FIG. 29 is a side view of a tensioner subassembly of the penile traction device of FIG. 28.

Referring also to FIG. 29, tensioner subassembly 720 includes a spring unit 726, a locking mechanism 725, and a contoured member 729. Spring unit 726 includes one or more compression springs that can supply, when in use, a distally-directed spring force from contoured member 729 to a user's penis. Locking mechanism 725 can be manually actuated to allow tensioner subassembly 720 to be slid along arms 715a and 715b. When locking mechanism 725 is unactuated, tensioner subassembly 720 is releasably locked in a particular position along arms 715a and 715b.

When used, the user's penis extends through base 710 and is clamped in clamp 750. The tensioner subassembly 720 is then slid distally until a desired amount of force from contoured member 729 is applied.

Figure 30:
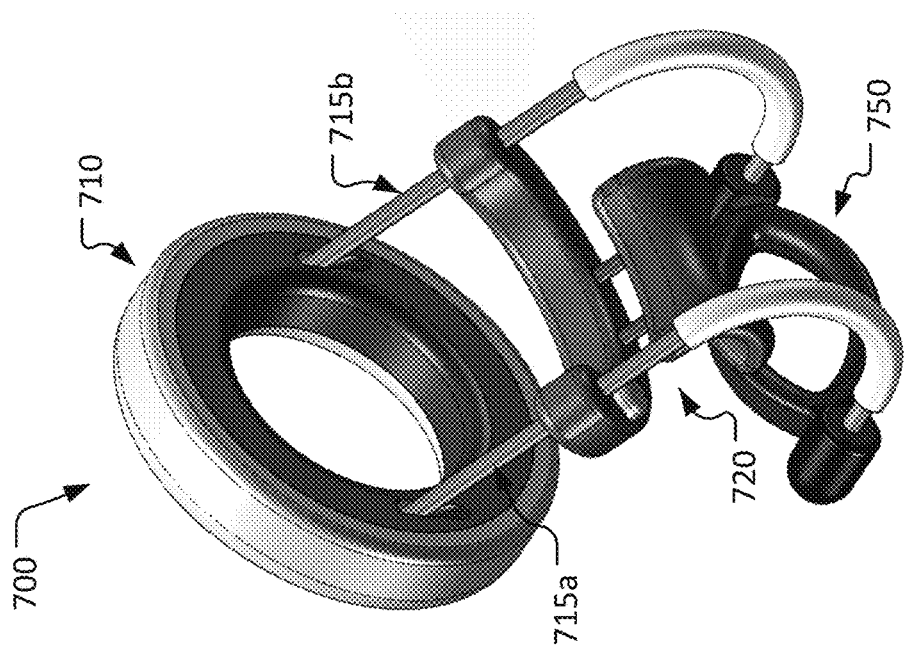
FIG. 30 is a perspective view of the penile traction device of FIG. 28 in a first configuration.

Referring now to FIG. 30, it may be advantageous in some cases to pivot arms 715a and 715b in relation to base 710. For example, the arrangement shown can add additional tensile force to the user's penis and allows for more discreet use. In some embodiments, arms 715a and 715b can be releasably latched in the desired orientation.

Figure 31:
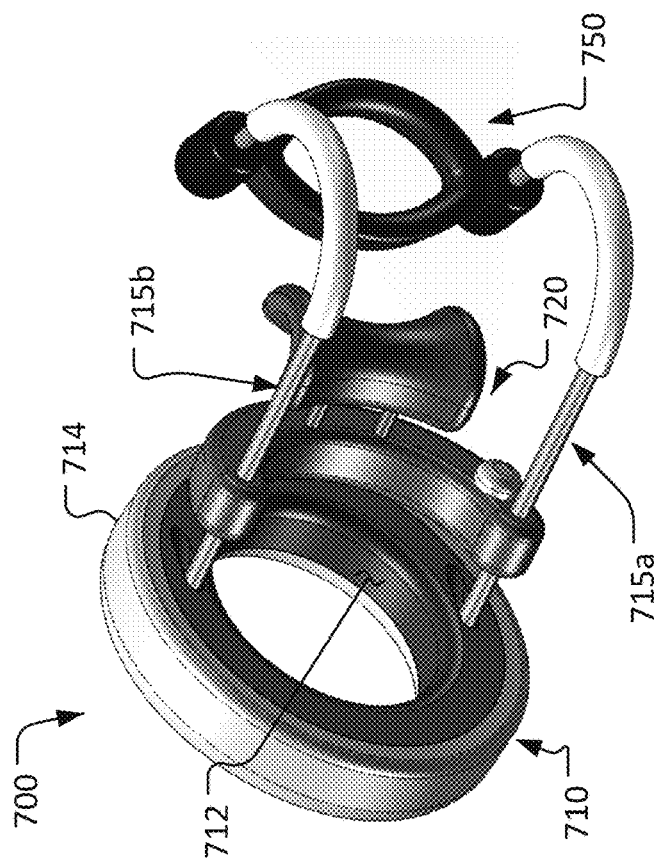
FIG. 31 is a perspective view of the penile traction device of FIG. 28 in a second configuration.

Referring now to FIG. 31, in some embodiments a lateral force (to counteract Peyronie's disease, for example) can be applied because base 710 can include an inner member 712 that is rotatable in relation to an outer member 714. In some such embodiments, inner member 712 can be releasably latched to outer member 714.

Figure 32:
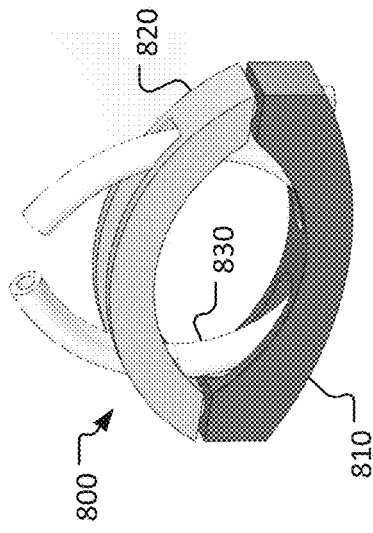
FIG. 32 is a perspective view of another example clamp subassembly, in a first configuration, that can be used in conjunction with the penile traction devices provided herein.
Figure 33:
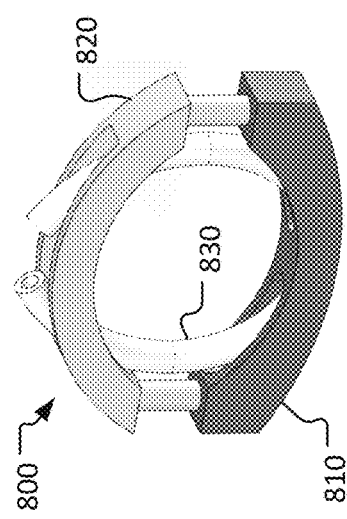
FIG. 33 is a perspective view of the clamp subassembly of FIG. 32 in a second configuration.

Referring to FIGS. 32 and 33, another example clamp assembly 800 is provided. Clamp assembly 800 can be used with the penile tractions devices provided herein.

Clamp assembly 800 includes a first clamp member 810, a second clamp member 820, and an elastomeric member 830. The first clamp member 810 is slidably coupled with the second clamp member 820. Elastomeric member 830 extends between clamp members 810 and 820, and provides the clamping force. Elastomeric member 830 is releasably attachable to second clamp member 820. Hence, when a desired clamping force is being delivered by clamp assembly 800, elastomeric member 830 can be attached to second clamp member 820 to maintain the clamping force.

Figure 34:
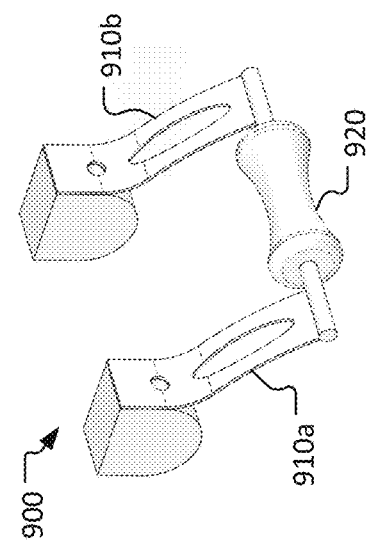
FIG. 34 is another example tensioner subassembly that can be used in conjunction with the penile traction devices provided herein.

Referring to FIG. 34, another example tensioner subassembly 900 is provided. Tensioner subassembly 900 can be used with the penile tractions devices provided herein.

Tensioner subassembly 900 includes leaf springs 910a and 910b that provide force to a user's penis via cambered roller 920.

Figure 35:
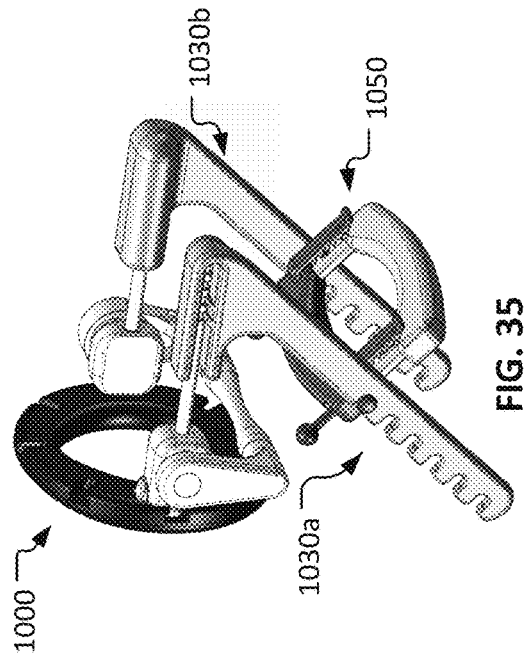
FIG. 35 is a perspective view of another example penile traction device in accordance with some embodiments provided herein.

Referring to FIG. 35, another example penile traction device 1000 is provided. Penile traction device 1000 includes angle arms 1030a and 1030b that define a series of notches with which clamp 500 can be selectively engaged to provide adjustability.

It should be understood that one or more features described in the context of a particular penile traction device embodiment provided herein can be combined with one or more features described in the context of another penile traction device embodiment provided herein. That is, features of the penile traction devices provided herein can be mixed and matched to create hybrid designs. Any and all such hybrid designs and combinations of features are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A penile traction device for applying traction force to a penis of a human body, the device comprising:
    a base, the base configured for interfacing with the human body while the traction force from the penile traction device is being applied to the penis;
    a frame extending from the base;
    a lateral traction member coupled to the frame, the lateral traction member adapted for contacting a middle portion of the penis to apply a lateral traction force to bend the middle portion of the penis; and
    a clamp coupled to the frame, the clamp configured for compressively clamping the penis.

2. The penile traction device of claim 1, wherein the frame comprises:
    a first extension rod that is releasably coupleable with the base at multiple locations on the base;
    a second extension rod that is releasably coupleable with the base at multiple locations on the base;
    a first angle arm that is releasably coupleable with the first extension rod at multiple locations on the first extension rod; and
    a second angle arm that is releasably coupleable with the second extension rod at multiple locations on the second extension rod.

3. The penile traction device of claim 2, wherein the clamp is coupled between the first angle arm and the second angle arm.

4. The penile traction device of claim 3, wherein the first angle arm defines a first angle arm track, the second angle arm defines a second angle arm track, and wherein the clamp is slidably engaged with each of the first angle arm track and the second angle arm track.

5. The penile traction device of claim 1, wherein the lateral traction member is slidably coupled to the frame.

6. A method of applying traction force to a penis, wherein the method comprises:
coupling the penile traction device of claim 1 to the penis; and
applying the traction force to the penis using the penile traction device.

7. The method of claim 6, wherein the traction force is applied subsequent to coupling the penile traction device to the penis.

8. The method of claim 6, wherein the traction force is a dynamic loading traction force.

9. The penile traction device of claim 1, wherein the lateral traction member comprises a roller.

10. The penile traction device of claim 9, wherein the cambered roller is pivotably coupled in relation to the frame.

11. The penile traction device of claim 1, wherein the clamp is slidably adjustable in relation to the frame.

12. The penile traction device of claim 1, wherein the clamp comprises a first clamp half and an opposing second clamp half.

13. The penile traction device of claim 12, wherein the first clamp half and the second clamp half define an opening there between, and wherein the first clamp half can be secured in relation to the second clamp half in a plurality of differing arrangements so as to define a plurality of differing sizes of the opening.

14. The penile traction device of claim 12, wherein the first clamp half and the second clamp half clamp each include a contoured duckbill surface for interfacing with the penis.

15. The penile traction device of claim 1, wherein the base defines a clearance hole through which the penis can extend.

16. The penile traction device of claim 1, wherein the base has a cushioned interface with the human body.

17. The method of claim 6, wherein the traction force comprises the lateral traction force.

18. The penile traction device of claim 1, wherein the lateral traction member comprises a contoured surface.

* * * * *

UNITED STATES PATENT AND TRADEMARK OFFICE
CERTIFICATE OF CORRECTION

| | |
|---|---|
| PATENT NO. | : 10,117,771 B2 |
| APPLICATION NO. | : 15/040364 |
| DATED | : November 6, 2018 |
| INVENTOR(S) | : Trost et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 230 days.

Signed and Sealed this
Fifth Day of March, 2019

Andrei Iancu
*Director of the United States Patent and Trademark Office*